United States Patent
Thiruvengadam et al.

(10) Patent No.: US 10,301,615 B2
(45) Date of Patent: May 28, 2019

(54) GENES EXPRESSED IN MENTAL ILLNESS AND MOOD DISORDERS

(71) Applicant: PSYCHNOSTICS, LLC, Baltimore, MD (US)

(72) Inventors: Alagu P. Thiruvengadam, Baltimore, MD (US); Krish Chandrasekaran, Baltimore, MD (US)

(73) Assignee: PsychNostics, LLC, Baltimore, MD (US)

( * ) Notice: Subject to any disclaimer, the term of this patent is extended or adjusted under 35 U.S.C. 154(b) by 652 days.

(21) Appl. No.: 14/763,706

(22) PCT Filed: Jan. 30, 2014

(86) PCT No.: PCT/US2014/013841
§ 371 (c)(1),
(2) Date: Jul. 27, 2015

(87) PCT Pub. No.: WO2014/133707
PCT Pub. Date: Sep. 4, 2014

(65) Prior Publication Data
US 2016/0002623 A1 Jan. 7, 2016

Related U.S. Application Data

(60) Provisional application No. 61/771,304, filed on Mar. 1, 2013.

(51) Int. Cl.
| | |
|---|---|
| *C12N 15/10* | (2006.01) |
| *C12Q 1/68* | (2018.01) |
| *C40B 30/04* | (2006.01) |
| *C40B 40/06* | (2006.01) |
| *C12Q 1/6883* | (2018.01) |
| *C12Q 1/6806* | (2018.01) |

(52) U.S. Cl.
CPC ....... *C12N 15/1034* (2013.01); *C12Q 1/6806* (2013.01); *C12Q 1/6883* (2013.01); *C12Q 2600/136* (2013.01); *C12Q 2600/158* (2013.01); *C40B 30/04* (2013.01); *C40B 40/06* (2013.01)

(58) Field of Classification Search
None
See application file for complete search history.

(56) References Cited

U.S. PATENT DOCUMENTS

| | | |
|---|---|---|
| 2004/0005631 A1 | 1/2004 | Lamb et al. |
| 2004/0248286 A1* | 12/2004 | Konradi et al. ..... C12Q 1/6837 435/287.2 |
| 2006/0051786 A1 | 3/2006 | Akil et al. |
| 2008/0009010 A1 | 1/2008 | Konradi |
| 2011/0014610 A1 | 1/2011 | Akil et al. |

OTHER PUBLICATIONS

International Search Report for PCT/US2014/013841 dated Jul. 9, 2014 [PCT/ISA/210].
Written Opinion for PCT/JP2014/013841 dated Jul. 9, 2014 [PCT/ISA/237].

* cited by examiner

*Primary Examiner* — Kaijiang Zhang
(74) *Attorney, Agent, or Firm* — Sughrue Mion, PLLC

(57) ABSTRACT

The present invention relates to a composition comprising a plurality of cDNA molecules for use in methods of detecting changes in expression of genes encoding proteins that are associated with mental illnesses and which are differentially expressed in patients with mental illnesses, such as bipolar I disorder, bipolar II disorder, unipolar disorder, schizophrenia, attention deficit hyperactive disorders, obsessive compulsive disorders, anxiety disorders or other related mood disorders. The composition and the cDNA molecules may be used in their entirety or in part as to diagnose, to stage, to treat, and/or to monitor the treatment of a subject with mental illness.

23 Claims, 8 Drawing Sheets
Specification includes a Sequence Listing.

GENES EXPRESSED IN MENTAL ILLNESS AND MOOD DISORDERS

CROSS REFERENCE TO RELATED APPLICATIONS

This application is a National Stage of International Application No. PCT/US2014/013841, filed on Jan. 30, 2014, which claims priority from U.S. Provisional Application No. 61/771,304, filed on Mar. 1, 2013, the contents of all of which are incorporated herein by reference in their entirety.

FIELD OF THE INVENTION

The present invention relates to a composition comprising a plurality of cDNA molecules for use in methods of detecting changes in expression of genes encoding proteins that are associated with mental illnesses and which are differentially expressed in patients with mental illnesses, such as bipolar I disorder, bipolar II disorder, unipolar disorder, schizophrenia, attention deficit hyperactive disorders, obsessive compulsive disorders, anxiety disorders or other related mood disorders. The composition and the cDNAs may be used in their entirety or in part as to diagnose, to stage, to treat, and/or to monitor the treatment of a subject with mental illness.

BACKGROUND OF THE INVENTION

Array technology can provide a simple way to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for examining which genes are tissue specific, carrying out housekeeping functions, parts of a signaling cascade, or specifically related to a particular genetic predisposition, condition, disease, or disorder.

The potential application of gene expression profiling is particularly relevant to improving diagnosis, prognosis, and treatment of disease. For example, both the levels of gene expression and the particular sequences expressed may be examined in tissues from subjects with mental illnesses such as bipolar I disorder, bipolar II disorder, unipolar disorder, schizophrenia, attention deficit hyperactive disorders, obsessive compulsive disorders, anxiety disorders or other related mood disorders, and compared with the levels of gene expression and the particular sequences expressed in normal tissue.

The Diagnostic and Statistical Manual (DSM-IV) published by the American Psychiatric Association serves as the basis for the description, identification and diagnosis of all the mental illnesses covered by this invention. These illnesses include bipolar I disorder, bipolar II disorder, unipolar disorder, attention deficit hyperactive disorder (ADHD) and schizophrenia. At present there are no biological markers to identify these illnesses individually or as a group. Membrane potentials have been used to diagnose bipolar I disorder, bipolar II disorder and ADHD and this technique is described in pending U.S. patent application Ser. No. 10/823,647 and U.S. provisional patent application No. 60/670,237.

The present invention provides for a composition comprising a plurality of cDNA molecules for use in methods of detecting changes in expression of genes encoding proteins that are associated with mental illnesses. Such a composition, and the cDNA molecules, can be employed for the diagnosis, prognosis and/or treatment of mental illnesses that are correlated with differential gene expression. Differential gene expression may also reflect inflammation, proliferation, and/or cell activation which occur secondary to the disease process. The present invention satisfies a need in the art in that it provides a set of differentially expressed genes which may be used entirely or in part to diagnose, to stage, to treat, and/or to monitor the progression or treatment of a subject with mental illnesses, such as bipolar disorder.

SUMMARY OF THE INVENTION

The present invention provides a composition comprising a plurality of cDNA molecules and their complements. The cDNA molecules of the composition are differentially expressed in vivo and are selected from SEQ ID NOs:1-50 as presented in the Sequence Listing. Earlier studies have shown that each cDNA molecule of SEQ ID NOs: 1-15 is either upregulated or down-regulated significantly among various mental illnesses. In one aspect, the composition is useful to diagnose mental illnesses such as bipolar I disorder, bipolar II disorder, unipolar disorder, schizophrenia, attention deficit hyperactive disorders, obsessive compulsive disorders, anxiety disorders or other related mood disorders, particularly through the use of blood. In another aspect, the composition is immobilized on a substrate.

The invention also provides a high throughput method to detect differential expression of one or more genes encoding proteins that are associated with a mental illnesses using the composition of the present invention. The method comprises exposing a substrate comprising the composition of the present invention to a test sample under conditions such that hybridization complexes form between at least one cDNA molecule of the composition and at least one polynucleotide in the test sample, detecting the hybridization complexes, and comparing the hybridization complexes with those of a standard, wherein differences in the size and signal intensity of each hybridization complex indicates differential expression of nucleic acids in the test sample. In one aspect, the test sample is from a subject with a mental illness and differential expression determines an early, mid, or late stage of that mental illness.

The invention further provides a high throughput method of screening a library of molecules or compounds to identify a ligand that binds a cDNA molecule of the composition of the present invention. The method comprises exposing a substrate comprising the composition of the present invention to a library of molecules or compounds under conditions to allow specific binding between at least one cDNA molecule in the composition and at least one molecule or compound, and detecting specific binding, thereby identifying a ligand that binds a cDNA molecule of the composition of the present invention. Libraries of molecules or compounds are selected from DNA molecules, RNA molecules, mimetics, peptides, transcription factors and other regulatory proteins.

The invention still further provides an isolated cDNA molecule selected from SEQ ID NOs: 1-15 as presented in the Sequence Listing. The invention also provides an expression vector comprising the cDNA molecule, a host cell transfected or transformed with the expression vector, and a method for producing a protein encoded by the cDNA molecule comprising culturing the host cell under conditions suitable for the expression of a protein encoded by the cDNA molecule and recovering the protein from the host cell culture. The invention additionally provides a method for purifying a ligand, the method comprising combining a cDNA molecule of the invention with a sample under conditions which allow specific binding between the cDNA molecule and a ligand in the sample, recovering the hound cDNA molecule, and separating the ligand from the cDNA molecule, thereby obtaining a purified ligand.

The present invention also provides a purified protein encoded by a cDNA molecule of the invention. The invention also provides a high-throughput method for using a protein encoded by a cDNA molecule of the invention to screen a library of molecules or compounds to identify a ligand that binds a protein encoded by a cDNA molecule of the invention. The method comprises combining the protein or a portion thereof with a library of molecules or compounds under conditions to allow specific binding between the protein or portion thereof, and a molecule or compound of the library, and detecting specific binding, thereby identifying a ligand which specifically binds the protein. Libraries of molecules or compounds are selected from DNA molecules, RNA molecules, PNAs, mimetics, peptides, proteins, agonists, antagonists, antibodies or their fragments, immunoglobulins, inhibitors, drug compounds, and pharmaceutical agents. The invention further provides for using a polypeptide encoded by a cDNA molecule of the invention to purify a ligand. The method comprises combining a protein or a portion thereof with a sample under conditions to allow specific binding between the protein or portion thereof, and a ligand in the sample, recovering the bound protein, and separating the protein from the ligand, thereby obtaining purified ligand. The invention still further provides a pharmaceutical composition comprising the protein. The invention yet still further provides a method for using the protein to produce an antibody. The method comprises immunizing an animal with the protein or an antigenically-effective portion thereof under conditions to elicit an antibody response, isolating animal antibodies, and screening the isolated antibodies with the protein to identify an antibody which specifically binds the protein.

BRIEF DESCRIPTION OF THE DRAWINGS

FIG. 1—BCO32245—This figure shows a comparison of the gene expression of ATP Synthase F0 subunit D in controls, bipolar I, ADHD, schizophrenia and unipolar blood samples. F0D is significantly downregulated in bipolar I and schizophrenia while it is significantly upregulated in unipolar. There is no significant difference in ADHD patient blood samples.

FIGS. 2—AA022514—This figure shows a comparison of the gene expression of ATP Synthase OSCP subunit in controls, bipolar I, ADHD, schizophrenia and unipolar blood samples. OSCP is significantly downregulated in bipolar I, schizophrenia and ADHD. There is no significant difference in unipolar patient blood samples.

FIG. 3—BC003678—This figure shows a comparison of the gene expression of ATP Synthase F0 subunit F in controls, bipolar I, ADHD, schizophrenia and unipolar blood samples. F0F is significantly downregulated in bipolar I and schizophrenia while it is significantly upregulated in unipolar. There is no significant difference in ADHD patient blood samples.

FIG. 4—NM_005011—This figure shows a comparison of the gene expression of nuclear respiratory factor-1 (NRF-1) in controls, bipolar I, ADHD, schizophrenia and unipolar blood samples. NRF-1 is significantly downregulated in bipolar I, ADHD and unipolar samples, while there is no significant difference in schizophrenic patient blood samples.

FIG. 5—NC_001807—This figure shows a comparison of the gene expression of COX I in controls, bipolar I, ADHD, schizophrenia and unipolar blood samples. COX I is significantly downregulated in bipolar I, unipolar and ADHD, while there is no significant difference in schizophrenia patient blood samples.

FIGS. 6—X13274—This figure shows a comparison of the gene expression of interferon-gamma (IFN-G) in controls, bipolar I, ADHD, schizophrenia and unipolar blood samples. IFN-gamma is significantly downregulated in ADHD and unipolars, there is no significant difference in bipolar I and schizophrenia patient blood samples.

FIG. 7—BC017176—This figure shows a comparison of the gene expression of inositol mono phosphatase (IMPase) in controls, bipolar I, ADHD, schizophrenia and unipolar blood samples. IMPase is significantly upregulated in unipolar, ADHD and schizophrenia while there is no significant difference in bipolar 1 patient blood samples.

FIGS. 8—AA447623—This figure shows a comparison of the gene expression of sorbitol dehydrogenase (SDH) in controls, bipolar I, ADHD, schizophrenic and unipolar blood samples. SDH is significantly upregulated in unipolar. There is no significant difference in bipolar I, schizophrenia and ADHD patient blood samples.

DETAILED DESCRIPTION OF THE INVENTION

Definitions

Figure 1:
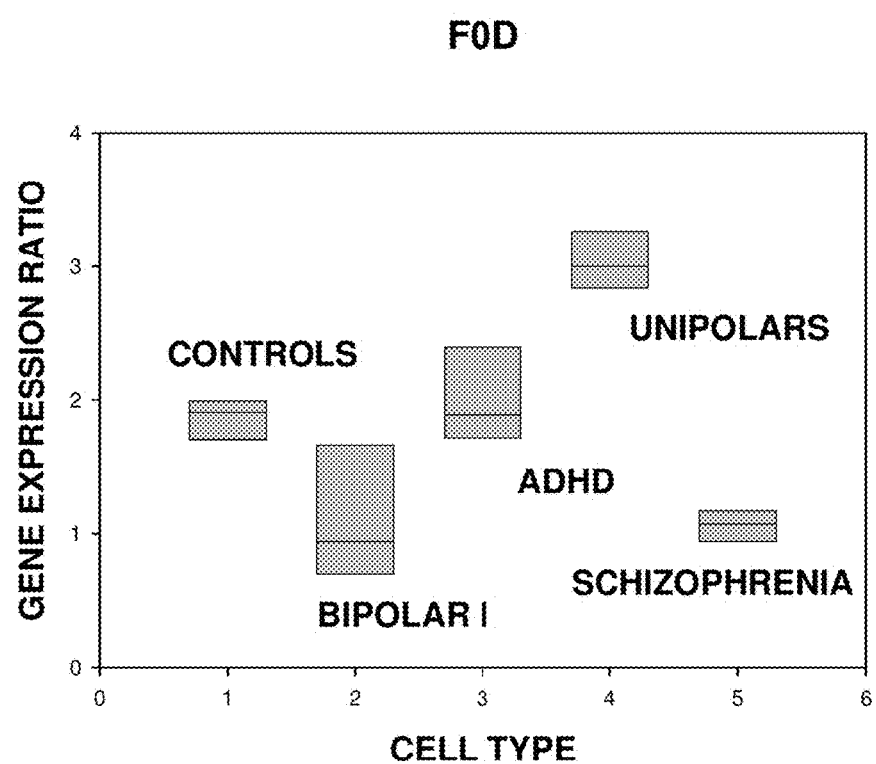
FIG. 1-8 are bar graphs that show changes in gene expression for different groups of functionally related genes. The relative percent of genes on the array with higher levels of expression in mental illness vs. controls is indicated with a grey bar, and the relative percent with lower levels of expression is indicated with a hatched bar.

"Array" refers to an ordered arrangement of cDNA molecules. The cDNA molecules are arranged on a substrate so that there are a "plurality" of cDNA molecules, preferably at least 10 cDNA molecules, more preferably at least 100 cDNA molecules, even more preferably from about 500 to about 1000 cDNA molecules, and most preferably at least 10,000 cDNA molecules. Furthermore, the arrangement of the cDNA molecules on the substrate assures that the size and signal intensity of each hybridization complex formed between a cDNA molecule and a sample nucleic acid is individually distinguishable. The number of cDNA molecules on the array is primarily related to the convenience of screening a large number of different cDNA molecules at the same time. The skilled artisan will understand that arrays having a small number of cDNA molecules, such as between 10 and 100, may be preferred depending on the experimental conditions and the assay being performed.

"cDNA molecule" refers to a chain of nucleotides, an isolated polynucleotide, nucleotide, nucleic acid molecule, or any fragment or complement thereof. It may have originated recombinantly or synthetically and be double-stranded or single-stranded, coding and/or noncoding, an exon or an intron of a genomic DNA molecule, or combined with carbohydrate, lipids, protein or inorganic elements or substances. The skilled artisan will understand that cDNA molecules may vary in length depending on the conditions under which the molecules are being used. For example, the chain may be between about 15 to about 10,000 nucleotides. Preferably, the cDNA molecules of the instant invention are between about 25 and 500 nucleotides in length, more preferably from about 100 to about 300 nucleotides and most preferably from about 150 to about 250 nucleotides.

The phrase "cDNA molecule encoding a protein" refers to a nucleic acid sequence that encodes one or more amino acid residues, a chain of amino acid residues, a peptide, a polypeptide or a protein. The phrase also refers to a nucleic acid sequence that closely aligns with sequences which encode conserved protein motifs or domains that were identified by employing analyses well known in the art. These analyses include Hidden Markov Models (HMMs) such as PFAM (Krogh (1994) J Mol Biol 235:1501-1531; Sonnhamer et al. (1988) Nucl Acids Res 26:320-322), BLAST (Basic Local Alignment Search Tool; Altschul (1993) J Mol Evol 36: 290-300; and Altschul et al. (1990) J Mol Biol 215:403-410), or other analytical tools such as BLIMPS (Henikoff et al. (1998) Nucl Acids Res 26:309-12). Additionally, the phrase may be associated with specific human metabolic processes, conditions, disorders, or diseases.

"Derivative" refers to a cDNA molecule or a protein that has been subjected to a chemical modification such as the replacement of a hydrogen by, for example, an acetyl, acyl, alkyl, amino, formyl, or morpholine group. Derivative cDNA molecules may encode proteins that retain the essential biological characteristics of naturally occurring proteins.

"Disorder" refers to conditions, diseases or syndromes of mental illness and includes bipolar I disorder, bipolar II disorder, unipolar disorder, schizophrenia, attention deficit hyperactive disorders, obsessive compulsive disorders, anxiety disorders or other related mood disorders as defined by DSM IV of the American Psychiatric Association.

"Fragment" refers to a chain of at least 18, 20, 25, 30, 35, 40, 50 or 100 consecutive nucleotides from any part of a cDNA molecule. Fragments may be used in PCR or hybridization technologies to identify related nucleic acid molecules and to screen for or to purify a ligand. Nucleic acids and their ligands identified in this manner are useful as therapeutics to regulate replication, transcription or translation.

A "hybridization complex" is formed between a cDNA molecule and a nucleic acid of a sample when the purines of one molecule hydrogen bond with the pyrimidines of the complementary molecule. In most cases, the molecules will be completely complementary, e.g., 5'-A-G-T-C-3' base pairs with 3'-T-C-A-G-5'.

"Ligand" refers to any agent, molecule, or compound which will bind specifically to a site on a cDNA molecule, polynucleotide, or protein. Such ligands stabilize or modulate the activity of cDNA molecules or proteins and may be composed of at least one of the following: inorganic and organic substances including nucleic acids, oligonucleotides, polynucleotides, amino acids, peptides, proteins, carbohydrates, fats, and lipids.

"Oligonucleotide" or "oligomer" refers to a nucleotide sequence of at least about 15 nucleotides to as many as about 60 nucleotides, preferably about 18 to 30 nucleotides, and most preferably about 20 to 25 nucleotides that are used as a "primer" or "amplimer" in the polymerase chain reaction (PCR) or as an array element, or in other manners well known to the skilled artisan.

"Portion" refers to any part of a protein used for any purpose; but especially, to an epitope for the screening or purification of ligands or for the production of antibodies.

"Post-translational modification" of a protein may involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA molecule or a fragment thereof that hybridizes to at least one nucleic acid molecule in a sample or on a substrate. Where the molecular targets are double stranded, the probes may be either sense or antisense strands. Where targets are single stranded, probes are complementary single strands. Probes can be operably linked to reporter molecules for use in hybridization reactions including Southern, northern, in situ, dot blot, array, and like technologies or in screening or purification assays.

"Protein" refers to a polypeptide or any portion thereof. A portion of a protein generally retains biological or immunogenic characteristics of a native protein. An "oligopeptide" is an amino acid sequence of at least about 5 residues, more preferably 10 residues and most preferably about 15 residues that is used as part of a fusion protein to produce an antibody.

"Purified" refers to any molecule or compound that is separated from its natural environment and is at least about 60% free, 70% free, 80% free, 90% free, preferably about 95% free, and most preferably about 99% free, from other components with which it is naturally associated.

"Sample" is used in its broadest sense. A sample containing nucleic acids, proteins, antibodies, and the like may comprise a bodily fluid such as blood; a soluble fraction of a cell preparation or media in which cells were grown; a chromosome, an organelle, or membrane isolated or extracted from a cell; genomic DNA, RNA, or cDNA in solution or bound to a substrate; a cell; a tissue; a tissue print; a fingerprint, skin or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding between two single stranded nucleic acids, or the binding between an epitope of a protein and an agonist, antagonist, or antibody.

"Substrate" refers to any rigid or semi-rigid support to which cDNA molecules or proteins are bound and includes membranes (such as nylon, nitrocellulose), polypropylene supports, glass supports, silicon supports, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA molecule or a protein encoded by the cDNA molecule. Splice variants may be determined by BLAST score, wherein the score is at least 100, and most preferably at least 400. Allelic variants have a high percent identity to the cDNA molecules and may differ, for example, by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid. Such changes may predispose an individual to a specific disease or condition. Variants also include polynucleotide having at least about 70%, 75%, 80%, 85%, 90%, 95%, 96%, 97%, 98% or 99% sequence identity with a reference polynucleotide. Similarly, variants also include polypeptides having at least about 70%, 75%, 80%, 85%, 90%, 95%, 96%, 97%, 98% or 99% sequence identity with a reference polypeptide.

The Invention

The present invention provides for a composition comprising a plurality of cDNA molecules or their complements, wherein the cDNA molecules are at least one of SEQ ID NOs:1-50, which may be used on a substrate to diagnose, to stage, to treat, and/or to monitor the progression or treatment of mental illnesses. These cDNA molecules represent known and novel genes differentially expressed in subjects with mental illness. The composition may be used in its entirety or in part, as subsets of either upregulated or downregulated cDNA molecules may be used, such as one or more of SEQ ID NOs:1-15, or one or more of SEQ ID NOs:1-8.

Table 1 shows those genes previously found to have either significantly higher or lower expression in samples from patients with bipolar I disorder, ADHD, unipolar disorder or schizophrenia. Column 1 shows the mental illness of the patent from which the sample was obtained, column 2 shows corresponding SEQ ID number, column 3 shows the identity of the gene being screened, column 4 shows the GenBank Accession Number for the gene in column 3, columns 5 and 6 indicated whether gene expression was upregulated or down-regulated.

TABLE 1

| ILLNESS | SEQ ID NO: | GENE | ACCESSION # | UPREGULATED | DOWNREGULATED |
|---|---|---|---|---|---|
| Bipolar 1 Disorder | 1 | F0D | BC032245 | | Yes |
| | 2 | OSCP | BC021233 | | Yes |
| | 3 | F0F | BC003678 | | Yes |
| | 4 | NRF-1 | NM_005011 | | Yes |
| | 5 | COX I | NC_001807 | | Yes |
| | 10 | TFAM | NM_003201 | | Yes |
| | 9 | COX-II | NC_001807 | | Yes |
| | 8 | SDH | L29008 | Yes | |
| | 7 | IMPase | BC017176 | Yes | |
| | 6 | IFN Gamma | X13274 | Yes | |
| | 11 | GFAP | BC013596 | Yes | |
| | 12 | HSP60 | BC002676 | Yes | |
| | 13 | LDH-B | BT019765 | Yes | |
| | 14 | HK | M75126 | Yes | |
| | 15 | GSK3 Beta | BC012760 | Yes | |
| ADHD | 1 | F0D | BC032245 | | Yes |
| | 2 | OSCP | BC021233 | | Yes |
| | 3 | F0F | BC003678 | | Yes |
| | 4 | NRF-1 | NM_005011 | | Yes |
| | 5 | COX I | NC_001807 | | Yes |
| | 10 | TFAM | NM_003201 | | Yes |
| | 9 | COX-II | NC_001807 | | Yes |
| | 8 | SDH | L29008 | Yes | |
| | 7 | IMPase | BC017176 | Yes | |
| | 6 | IFN Gamma | X13274 | Yes | |
| | 11 | GFAP | BT019765 | Yes | |
| | 12 | HSP60 | BC002676 | Yes | |
| | 13 | LDH-B | BT019765 | Yes | |
| | 14 | HK | M75126 | Yes | |
| | 15 | GSK3 Beta | BC012760 | Yes | |
| Unipolar | 1 | F0D | BC032245 | Yes | |
| | 2 | OSCP | BC021233 | Yes | |
| | 3 | F0F | BC003678 | Yes | |
| | 4 | NRF-1 | NM_005011 | Yes | |
| | 5 | COX I | NC_001807 | Yes | |
| | 10 | TFAM | NM_003201 | Yes | |
| | 9 | COX-II | NC_001807 | Yes | |
| | 8 | SDH | L29008 | | Yes |
| | 7 | IMPase | BC017176 | | Yes |
| | 6 | IFN Gamma | X13274 | | Yes |
| | 11 | GFAP | BT019765 | | Yes |
| | 12 | HSP60 | BC002676 | | Yes |
| | 13 | LDH-B | BT019765 | | Yes |
| | 14 | HK | M75126 | | Yes |
| | 15 | GSK3 Beta | BC012760 | | Yes |
| Schizophrenia | 1 | F0D | BC032245 | Yes | |
| | 2 | OSCP | BC021233 | Yes | |
| | 3 | F0F | BC003678 | Yes | |
| | 4 | NRF-1 | NM_005011 | Yes | |
| | 5 | COX I | NC_001807 | Yes | |
| | 10 | TFAM | NM_003201 | Yes | |
| | 9 | COX-II | NC_001807 | Yes | |
| | 8 | SDH | L29008 | Yes | |
| | 7 | IMPase | BC017176 | Yes | |
| | 6 | IFN Gamma | X13274 | Yes | |
| | 11 | GFAP | BT019765 | Yes | |
| | 12 | HSP60 | BC002676 | Yes | |
| | 13 | LDH-B | BT019765 | Yes | |
| | 14 | HK | M75126 | Yes | |
| | 15 | GSK3 Beta | BC012760 | Yes | |

Figure 2:
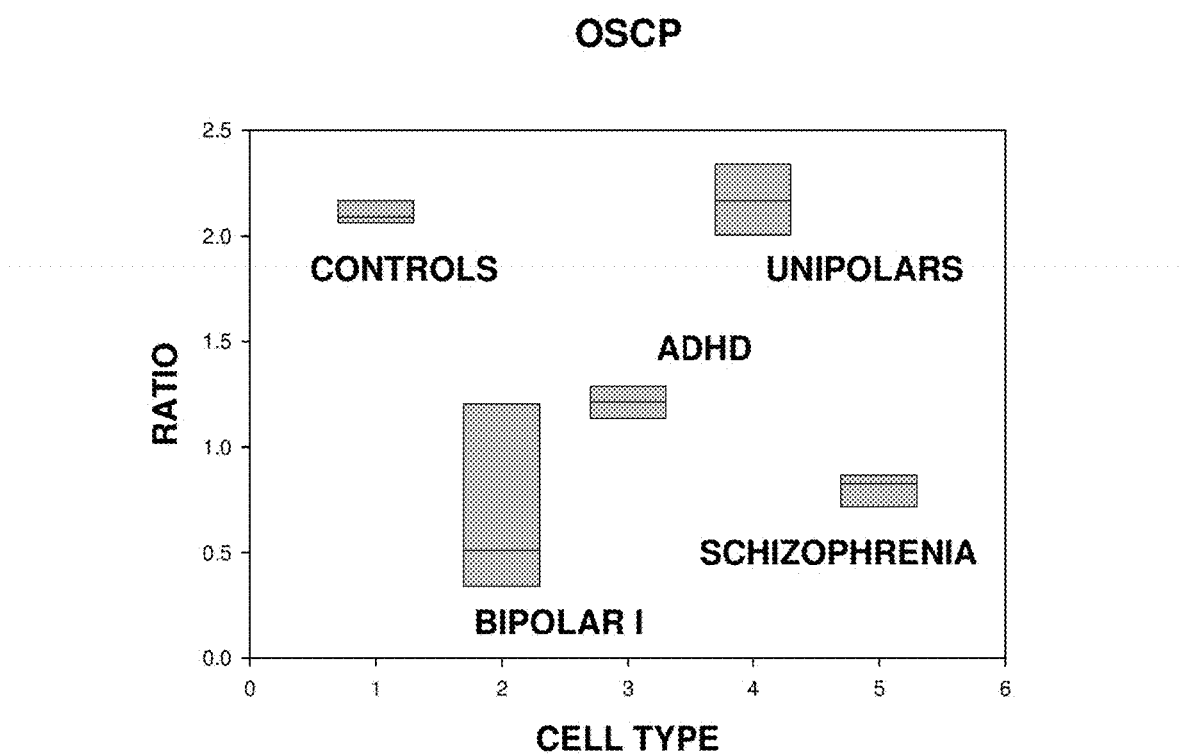
Figure 3:
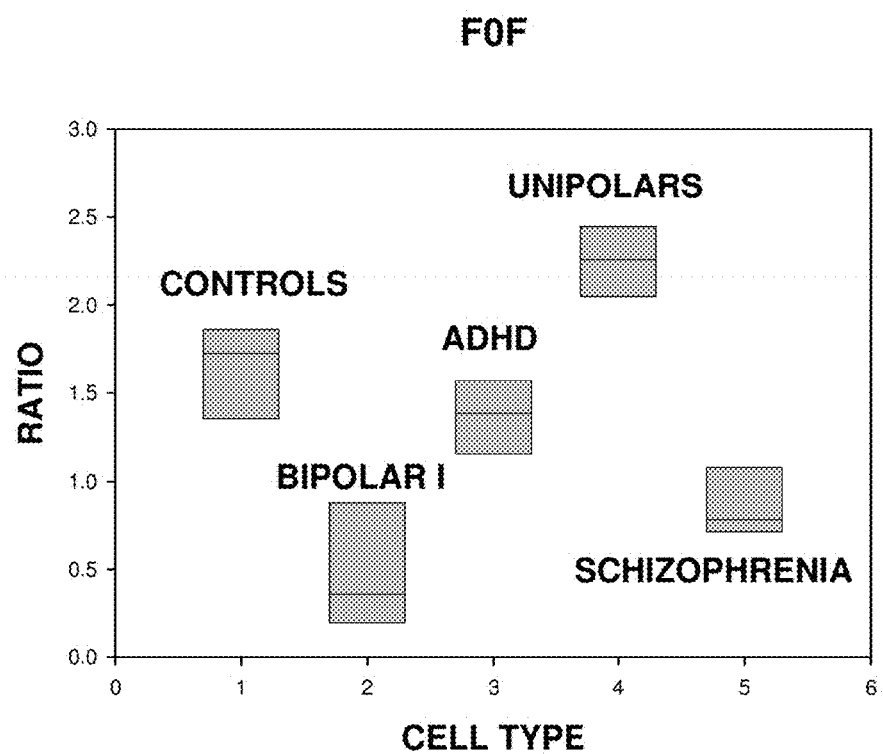
Figure 4:
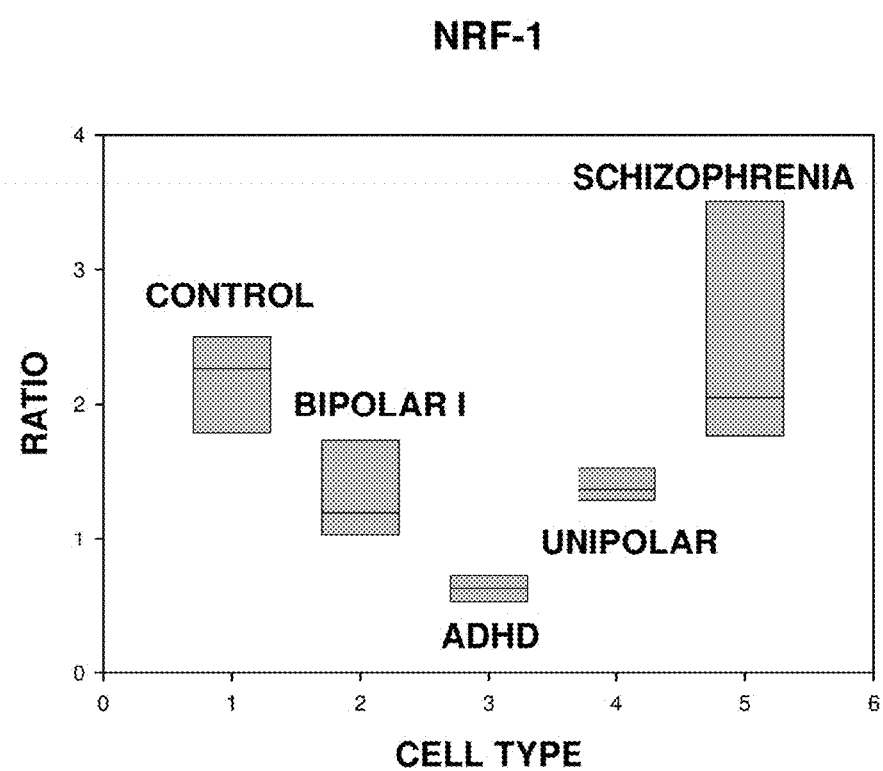
Figure 5:
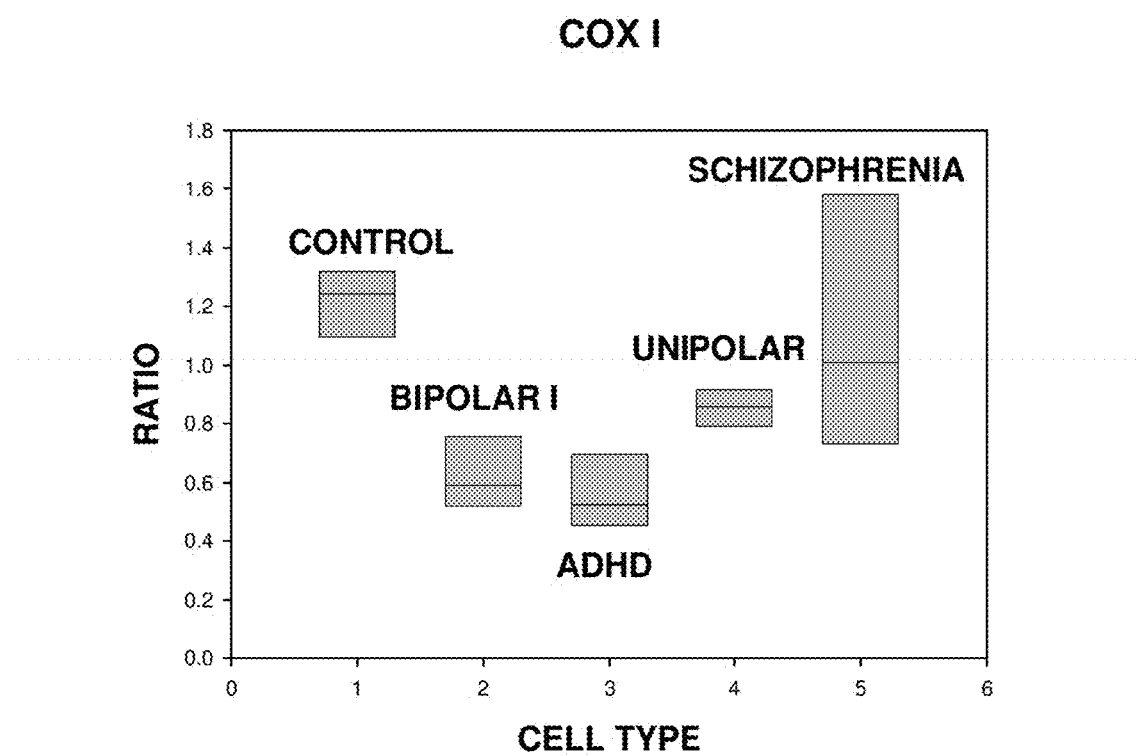
Figure 6:
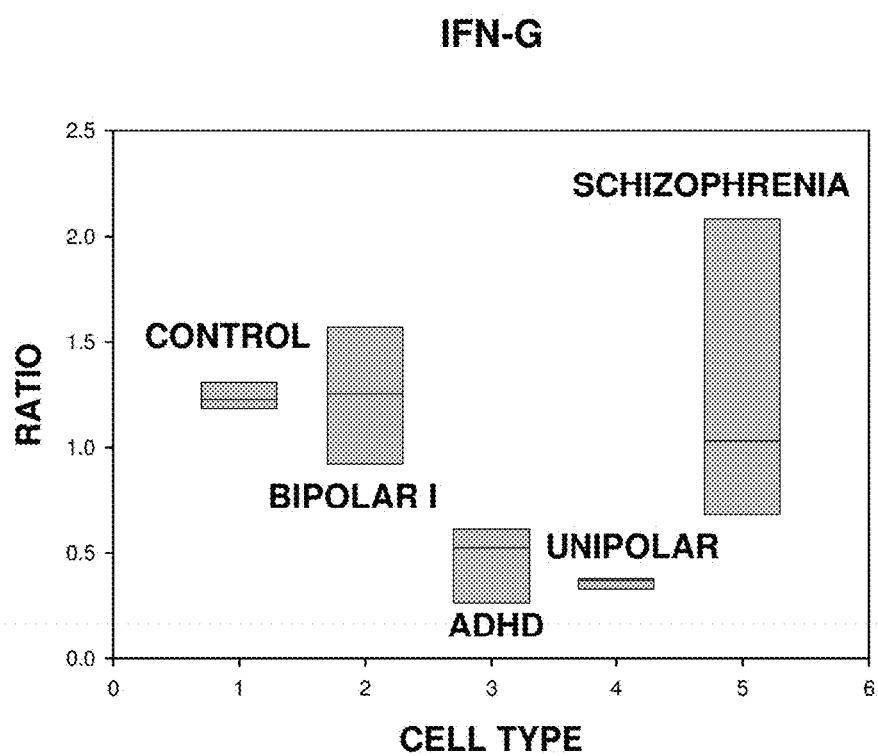
Figure 7:
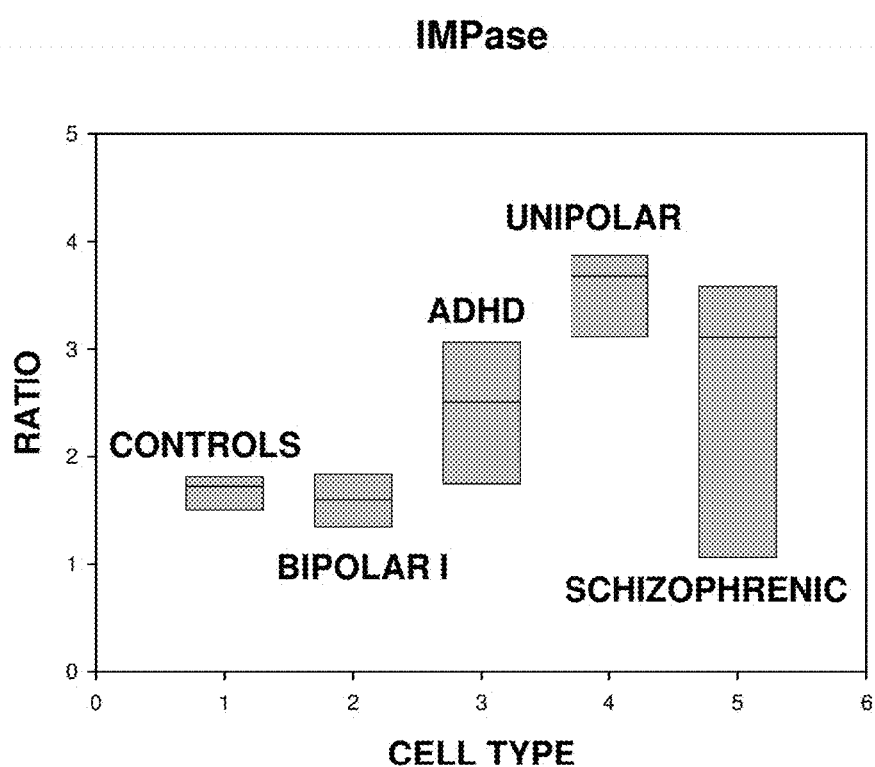
Figure 8:
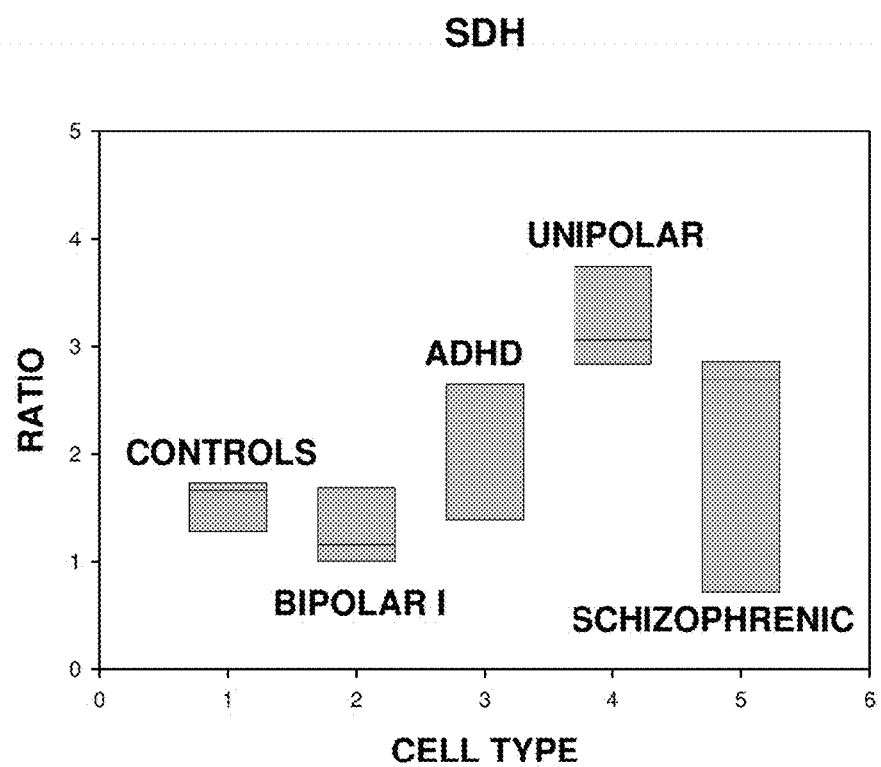

FIGS. 1-8 show functional differences in gene expression that are associated with mental illnesses. Genes were categorized by their likely function in the blood cells by surveying Genbarik accession number and name for both nucleotide and amino acid sequences, as well as surveying the scientific literature on each gene.

The cDNA molecules of the invention define a differential expression pattern against which to compare the expression pattern of the corresponding genes in a subject. Experimentally, differential expression of the cDNA molecules can be evaluated by methods including, but not limited to, differential display by spatial immobilization or by gel electrophoresis, genome mismatch scanning, representational discriminant analysis, clustering, transcript imaging, and array technologies. Differential expression can also be analyzed by quantitative or real-time RT-PCR (Reverse Transcriptase-Polymerase Chain Reaction) analysis using gene-specific oligonucleotides. "Oligonucleotide" or "oligomer" refers to a nucleotide sequence of at least about 15 nucleotides to as many as about 60 nucleotides, preferably about 18 to 30 nucleotides, and most preferably about 20 to 25 nucleotides that are used as a "primer" or "amplimer" in the RT-PCR reaction. These methods may be used alone or in combination.

The composition may be arranged on a substrate and hybridized with samples from subjects with diagnosed mental illness to identify those sequences which are differentially expressed in mental illnesses. This allows identification of those sequences of highest diagnostic and potential therapeutic value. In a third aspect, the composition is arranged on a substrate with an additional set of cDNA molecules, such as cDNAs molecule encoding signaling molecules. Such combinations may be useful in the elucidation of pathways which are affected in a particular mental disorder or to identify new, co-expressed, candidate, therapeutic molecules.

In a fourth aspect, the composition can be used for large scale genetic or gene expression analysis of a large number of novel, nucleic acid molecules. These samples are prepared by methods well known in the art and are from mammalian cells or tissues which are in a certain stage of development; have been treated with a known molecule or compound, such as a cytokine, growth factor, a drug, and the like; or have been extracted or biopsied from a mammal with a known or unknown condition, disorder, or disease before or after treatment. The sample nucleic acid molecules are hybridized to the composition for the purpose of defining a novel gene profile associated with that developmental stage, treatment, or disorder.

cDNA Molecules and their Use cDNA molecules can be prepared by a variety of synthetic or enzymatic methods well known in the art. cDNA molecules can be synthesized, in whole or in part, using chemical methods well known in the art (Caruthers et al. (1980) Nucleic Acids Symp. Ser. (7)215-233). Alternatively, cDNA molecules can be produced enzymatically or recombinantly, by in vitro or in vivo transcription.

Nucleotide analogs can be incorporated into cDNA molecules by methods well known in the art. The only requirement is that the incorporated analog must base pair with native purines or pyrimidines. For example, 2,6-diaminopurine can substitute for adenine and form stronger bonds with thymidine than those between adenine and thymidine. A weaker pair is formed when hypoxanthine is substituted for guanine and base pairs with cytosine. Additionally, cDNA molecules can include nucleotides that have been derivatized chemically or enzymatically.

cDNA molecules can be synthesized on a substrate. Synthesis on the surface of a substrate may be accomplished using a chemical coupling procedure and a piezoelectric printing apparatus as described by Baldeschweiler et al. (PCT publication WO95/251116). Alternatively, the cDNA molecules can be synthesized on a substrate surface using a self-addressable electronic device that controls when reagents are added as described by Heller et al. (U.S. Pat. No. 5,605,662). cDNA molecules can be synthesized directly on a substrate by sequentially dispensing reagents for their synthesis on the substrate surface or by dispensing preformed DNA fragments to the substrate surface. Typical dispensers include a micropipette delivering solution to the substrate with a robotic system to control the position of the micropipette with respect to the substrate. There can be a multiplicity of dispensers so that reagents can be delivered to the reaction regions efficiently.

cDNA molecules can be immobilized on a substrate by covalent means such as by chemical bonding procedures or UV irradiation. In one method, a cDNA molecule is bound to a glass surface which has been modified to contain epoxide or aldehyde groups. In another method, a cDNA molecule is placed on a polylysine coated surface and UV cross-linked to it as described by Shalon et al. (WO95/35505). In yet another method, a cDNA molecule is actively transported from a solution to a given position on a substrate by electrical means (Heller, supra). cDNA molecules do not have to be directly bound to the substrate, but rather can be bound to the substrate through a linker group. The linker groups are typically about 6 to 50 atoms long to provide exposure of the attached cDNA molecule. Preferred linker groups include ethylene glycol oligomers, diamines, diacids and the like. Reactive groups on the substrate surface react with a terminal group of the linker to bind the linker to the substrate. The other terminus of the linker is then bound to the cDNA molecule. Alternatively, polynucleotides, plasmids or cells can be arranged on a filter. In the latter case, cells are lysed, proteins and cellular components degraded, and the DNA is coupled to the filter by UV cross-linking.

The cDNA molecules may be used for a variety of purposes. For example, the composition of the invention may be used on a microarray. The microarray, in turn, can be used in high-throughput methods for detecting a related polynucleotide in a sample, screening libraries of molecules or compounds to identify a ligand, diagnosing a particular brain disorder, or inhibiting or inactivating a therapeutically relevant gene related to the cDNA molecule.

When the cDNA molecules of the invention are employed on a microarray, the cDNA molecules are organized in an ordered fashion so that each cDNA molecule is present at a specified location on the substrate. Because the cDNA molecules are at specified locations on the substrate, the hybridization patterns and intensities, which together create a unique expression profile, can be interpreted in terms of expression levels of particular genes and can be correlated with a particular metabolic process, condition, disorder, disease, stage of disease, or treatment.

Hybridization

The cDNA molecules or fragments or complements thereof may be used in various hybridization technologies. The cDNA molecules may be labeled using a variety of reporter molecules by either PCR, recombinant, or enzymatic techniques. For example, a commercially available vector containing the cDNA molecule is transcribed in the presence of an appropriate polymerase, such as T7 or SP6 polymerase, and at least one labeled nucleotide. Commercial kits are available for labeling and cleanup of such cDNA molecules. Radioactive (Amersham Pharmacia Biotech (APB), Piscataway N.J.), fluorescent (Operon Technologies, Alameda Calif.), and chemiluminescent labeling (Promega, Madison Wis.) are well known in the art.

A cDNA molecule may represent the complete coding region of an mRNA molecule or be designed or derived from unique regions of the mRNA molecule or genomic molecule, an intron, a 3' untranslated region, or from a conserved motif. The cDNA molecule is at least 18 contiguous nucleotides in length and is usually single stranded. Such a cDNA molecule may be used under hybridization conditions that allow binding only to an identical sequence, a naturally occurring molecule encoding the same protein, or an allelic variant. Discovery of related human and mammalian sequences may also be accomplished using a pool of degenerate cDNA molecules and appropriate hybridization conditions. Generally, a cDNA molecule for use in Southern or northern hybridizations may be from about 400 to about 5000 nucleotides long. Such cDNA molecules have high binding specificity in solution-based or substrate-based hybridizations. An oligonucleotide, a fragment the cDNA molecule, may be used to detect a polynucleotide in a sample using PCR.

The stringency of hybridization is determined by G+C content of the cDNA molecule, salt concentration, and temperature. In particular, stringency is increased by reducing the concentration of salt or raising the hybridization temperature. In solutions used for some membrane based hybridizations, addition of an organic solvent such as formamide allows the reaction to occur at a lower temperature. Hybridization may be performed with buffers, such as 5× saline sodium citrate (SSC) with 1% sodium dodecyl sulfate (SDS) at 60° C., that permits the formation of a hybridization complex between nucleic acid sequences that contain some mismatches. Subsequent washes are performed with buffers such as 0.2×SSC with 0.1% SDS at either 45° C. (medium stringency) or 65°-68° C. (high stringency). At high stringency, hybridization complexes will remain stable only where the nucleic acid molecules are completely complementary. In some membrane-based hybridizations, preferably 35% or most preferably 50%, formamide may be added to the hybridization solution to reduce the temperature at which hybridization is performed. Background signals may be reduced by the use of detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel (supra, pp. 6.11-6.19, 14.11-14.36, and A1-43).

Dot-blot, slot-blot, low density and high density arrays are prepared and analyzed using methods known in the art. The skilled artisan will understand that cDNA molecules may vary in length depending on the conditions under which the molecules are being used. For example, cDNA molecules from about 18 consecutive nucleotides to about 5000 consecutive nucleotides in length are contemplated by the invention and used in array technologies. Preferably, the cDNA molecules of the instant invention are between about 25 and 500 nucleotides, more preferably from about 100 to about 300 nucleotides in length, and most preferably from about 150 to about 250 nucleotides.

The array may be used to monitor the expression level of large numbers of genes simultaneously and to identify genetic variants, mutations, and SNPs. Such information may be used to determine gene function; to understand the genetic basis of a disorder; to diagnose a disorder; and to develop and monitor the activities of therapeutic agents being used to control or cure a disorder. (See, e.g., U.S. Pat. No. 5,474,796; WO95/11995; WO95/35505; U.S. Pat. Nos. 5,605,662; and 5,958,342.)

Screening and Purification Assays

A cDNA molecule may be used to screen a library or a plurality of molecules or compounds for a ligand which specifically binds the cDNA molecule. Ligands may be DNA molecules, RNA molecules, PNAs, peptides, proteins such as transcription factors, promoters, enhancers, repressors, and other proteins that regulate replication, transcription, or translation of the polynucleotide in the biological system. The assay involves combining the cDNA molecule or a fragment thereof with the molecules or compounds under conditions that allow specific binding and detecting the bound cDNA molecule to identify at least one ligand that specifically binds the cDNA molecule.

In one embodiment, the cDNA molecule may be incubated with a library of isolated and purified molecules or compounds and binding activity determined by methods such as a gel-retardation assay (U.S. Pat. No. 6,010,849) or a reticulocyte lysate transcriptional assay. In another embodiment, the cDNA molecule may be incubated with nuclear extracts from biopsied and/or cultured cells and tissues. Specific binding between the cDNA molecule and a molecule or compound in the nuclear extract is initially determined by gel shift assay. Protein binding may be confirmed by raising antibodies against the protein and adding the antibodies to the gel-retardation assay where specific binding will cause a supershift in the assay.

In another embodiment, the cDNA molecule may be used to purify a molecule or compound using affinity chromatography methods well known in the art. In one embodiment, the cDNA molecule is chemically reacted with cyanogen bromide groups on a polymeric resin or gel. Then a sample is passed over and reacts with or binds to the cDNA molecule. The molecule or compound which is bound to the cDNA molecule may be released from the cDNA molecule by increasing the salt concentration of the flow-through medium and collected.

The cDNA molecule may be used to purify a ligand from a sample. A method for using a cDNA molecule to purify a ligand would involve combining the cDNA molecule or a fragment thereof with a sample under conditions to allow specific binding, recovering the bound cDNA molecule, and using an appropriate agent to separate the cDNA molecule from the purified ligand.

Protein Production and Uses

The full length cDNA molecules or fragment thereof may be used to produce purified proteins using recombinant DNA technologies (Ausubel (supra; pp. 16.1-16.62)). One of the advantages of producing proteins by these procedures is the ability to obtain highly-enriched sources of the proteins thereby simplifying purification procedures.

The proteins may contain amino acid substitutions, deletions or insertions made on the basis of similarity in polarity, charge, solubility, hydrophobicity, hydrophilicity, and/or the amphipathic nature of the residues involved. Such substitutions may be conservative in nature when the substituted residue has structural or chemical properties similar to the original residue (e.g., replacement of leucine with isoleucine or valine) or they may be non-conservative when the replacement residue is radically different (e.g., a glycine replaced by a tryptophan). Computer programs included in LASERGENE software (DNASTAR, Madison Wis.), MACVECTOR software (Genetics Computer Group, Madison Wis.) and RasMol software (www.umass.edu/microbio/rasmol) may be used to help determine which and how many amino acid residues in a particular portion of the protein may be substituted, inserted, or deleted without abolishing biological or immunological activity.

Expression of Encoded Proteins

Expression of a particular cDNA molecule may be accomplished by cloning the cDNA molecule into a vector and transforming this vector into a host cell. The cloning vector used for the construction of cDNA libraries in the LIFESEQ databases may also be used for expression. Such vectors usually contain a promoter and a polylinker useful for cloning, priming, and transcription. An exemplary vector may also contain the promoter for β-galactosidase, an amino-terminal methionine and the subsequent seven amino acid residues of β-galactosidase. The vector may be transformed into competent *E. coli* cells. Induction of the isolated bacterial strain with isopropylthiogalactoside (IPTG) using standard methods will produce a fusion protein that contains an N terminal methionine, the first seven residues of β-galactosidase, about 15 residues of linker, and the protein encoded by the cDNA molecule.

The cDNA molecule may be shuttled into other vectors known to be useful for expression of protein in specific hosts. Oligonucleotides containing cloning sites and fragments of DNA sufficient to hybridize to stretches at both ends of the cDNA molecule may be chemically synthesized by standard methods. These primers may then be used to amplify the desired fragments by PCR. The fragments may be digested with appropriate restriction enzymes under standard conditions and isolated using gel electrophoresis. Alternatively, similar fragments are produced by digestion of the cDNA molecule with appropriate restriction enzymes and filled in with chemically synthesized oligonucleotides. Fragments of the coding sequence from more than one gene may be ligated together and expressed.

Signal sequences that dictate secretion of soluble proteins are particularly desirable as component parts of a recombinant sequence. For example, a chimeric protein may be expressed that includes one or more additional purification-facilitating domains. Such domains include, but are not limited to, metal-chelating domains that allow purification on immobilized metals, protein A domains that allow purification on immobilized immunoglobulin, and the domain utilized in the FLAGS extension/affinity purification system (Immunex, Seattle Wash.). The inclusion of a cleavable-linker sequence such as ENTEROKINASEMAX (Invitrogen, San Diego Calif.) between the protein and the purification domain may also be used to recover the protein.

Suitable host cells may include, but are not limited to, mammalian cells such as Chinese Hamster Ovary (CHO) and human 293 cells, insect cells such as Sf9 cells, plant cells such as *Nicotiana tabacum*, yeast cells such as *Saccharomyces cerevisiae*, and bacteria such as *E. coli*. For each of these cell systems, a useful expression vector may also include an origin of replication and one or two selectable markers to allow selection in bacteria as well as in a transformed eukaryotic host. Vectors for use in eukaryotic expression hosts may require the addition of 3' poly(A) tail if the cDNA lacks poly(A).

Additionally, the vector may contain promoters or enhancers that increase gene expression. Many promoters are known and used in the art. Most promoters are host specific and exemplary promoters includes SV40 promoters for CHO cells; T7 promoters for bacterial hosts; viral promoters and enhancers for plant cells; and PGH promoters for yeast. Adenoviral vectors with the rous sarcoma virus enhancer or retroviral vectors with long terminal repeat promoters may be used to drive protein expression in mammalian cell lines. Once homogeneous cultures of recombinant cells are obtained, large quantities of secreted soluble protein may be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, and the like.

In addition to recombinant production, proteins or portions thereof may be produced manually, using solid-phase techniques (Stewart et al. (1969) Solid-Phase Peptide Synthesis, WH Freeman, San Francisco Calif.; Merrifield (1963) J Am Chem Soc 5:2149-2154), or using machines such as the ABI 431A peptide synthesizer (PE Biosystems, Norwalk Conn.). Proteins produced by any of the above methods may be used as pharmaceutical compositions to treat disorders associated with null or inadequate expression of the genomic sequence.

Screening and Purification Assays

A protein or a portion thereof encoded by the cDNA molecule may be used to screen libraries or a plurality of molecules or compounds for a ligand with specific binding affinity or to purify a molecule or compound from a sample. The protein or portion thereof employed in such screening may be free in solution, affixed to an abiotic or biotic substrate, or located intracellularly. For example, viable or fixed prokaryotic host cells that are stably transformed with recombinant nucleic acids that have expressed and positioned a protein on their cell surface can be used in screening assays. The cells are screened against libraries or a plurality of ligands and the specificity of binding or formation of complexes between the expressed protein and the ligand may be measured. The ligands may be DNA, RNA, or PNA molecules, agonists, antagonists, antibodies, immunoglobulins, inhibitors, peptides, pharmaceutical agents, proteins, drugs, or any other test molecule or compound that specifically binds the protein. An exemplary assay involves combining the mammalian protein or a portion thereof with the molecules or compounds under conditions that allow specific binding and detecting the bound protein to identify at least one ligand that specifically binds the protein.

This invention also contemplates the use of competitive drug screening assays in which neutralizing antibodies capable of binding the protein specifically compete with a test compound capable of binding to the protein or oligopeptide or fragment thereof. One method for high throughput screening using very small assay volumes and very small amounts of test compound is described in U.S. Pat. No. 5,876,946. Molecules or compounds identified by screening may be used in a model system to evaluate their toxicity, diagnostic, or therapeutic potential.

The protein may be used to purify a ligand from a sample. A method for using a protein to purify a ligand would involve combining the protein or a portion thereof with a sample under conditions to allow specific binding, recovering the bound protein, and using an appropriate chaotropic agent to separate the protein from the purified ligand.

Production of Antibodies

A protein encoded by a cDNA molecule of the invention may be used to produce specific antibodies. Antibodies may be produced using an oligopeptide or a portion of the protein with inherent immunological activity. Methods for producing antibodies include: 1) injecting an animal, usually goats, rabbits, or mice, with the protein, or an antigenically effective portion or an oligopeptide thereof, to induce an immune response; 2) engineering hybridomas to produce monoclonal antibodies; 3) inducing in vivo production in the lymphocyte population; or 4) screening libraries of recombinant immunoglobulins. Recombinant immunoglobulins may be produced as taught in U.S. Pat. No. 4,816,567.

Antibodies produced using the proteins of the invention are useful for the diagnosis of prepathologic disorders as well as the diagnosis of chronic or acute diseases characterized by abnormalities in the expression, amount, or distribution of the protein, A variety of protocols for competitive binding or immunoradiometric assays using either polyclonal or monoclonal antibodies specific for proteins are well known in the art. Immunoassays typically involve the formation of complexes between a protein and its specific binding molecule or compound and the measurement of complex formation.

Immunoassay procedures may be used to quantify expression of the protein in cell cultures, in subjects with a particular disorder or in model animal systems under various conditions. Increased or decreased production of proteins as monitored by immunoassay may contribute to knowledge of the cellular activities associated with developmental pathways, engineered conditions or diseases, or treatment efficacy. The quantity of a given protein in a given tissue may be determined by performing immunoassays on freeze-thawed detergent extracts of biological samples and comparing the slope of the binding curves to binding curves generated by purified protein.

Labeling of Molecules for Assay

A wide variety of reporter molecules and conjugation techniques are known by those skilled in the art and may be used in various cDNA, polynucleotide, protein, peptide or antibody assays. Synthesis of labeled molecules may be achieved using commercial kits for incorporation of a labeled nucleotide such as $^{32}$P-dCTP, Cy3-dCTP or Cy5-dCTP or amino acid such as $^{35}$S-methionine. Polynucleotides, cDNAs, proteins, or antibodies may be directly labeled with a reporter molecule by chemical conjugation to amines, thiols and other groups present in the molecules using reagents such as BIODIPY or FITC (Molecular Probes, Eugene Oreg.).

The proteins and antibodies may be labeled for purposes of assay by joining them, either covalently or noncovalently, with a reporter molecule that provides for a detectable signal. A wide variety of labels and conjugation techniques are known and have been reported in the scientific and patent literature including, but not limited to U.S. Pat. Nos. 3,817,837; 3,850,752; 3,939,350; 3,996,345; 4,277,437; 4,275,149; and 4,366,241.

Diagnostics

The cDNA molecules, or fragments thereof, may be used to detect and quantify altered gene expression; absence, presence, or excess expression of mRNAs; or to monitor mRNA levels during therapeutic intervention. Disorders associated with altered expression include bipolar I disorder, bipolar II disorder, unipolar disorder, schizophrenia, attention deficit hyperactive disorders, obsessive compulsive disorders, anxiety disorders or other related mood disorders. These cDNA molecules can also be utilized as markers of treatment efficacy against the diseases noted above and other mental illnesses, conditions, and diseases over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

For example, the cDNA molecule may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Gene Expression Profiles

A gene expression profile comprises a plurality of cDNA molecules and a plurality of detectable hybridization complexes, wherein each complex is formed by hybridization of one or more probes to one or more complementary sequences in a sample. The cDNA composition of the invention is used as elements on a microarray to analyze gene expression profiles. In one embodiment, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the microarray is employed to improve the treatment regimen. A dosage is established that causes a change in genetic expression patterns indicative of successful treatment. Expression patterns associated with the onset of undesirable side effects are avoided. This approach may be more sensitive and rapid than waiting for the patient to show inadequate improvement, or to manifest side effects, before altering the course of treatment.

In another embodiment, animal models which mimic a human disease can be used to characterize expression profiles associated with a particular condition, disorder or disease or treatment of the condition, disorder or disease. Novel treatment regimens may be tested in these animal models using microarrays to establish and then follow expression profiles over time. In addition, microarrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Assays Using Antibodies

Antibodies directed against epitopes on a protein encoded by a cDNA molecule of the invention may be used in assays to quantify the amount of protein found in a particular human cell. Such assays include methods utilizing the antibody and a label to detect expression level under normal or disease conditions. The antibodies may be used with or without modification, and labeled by joining them, either covalently or noncovalently, with a labeling moiety.

Protocols for detecting and measuring protein expression using either polyclonal or monoclonal antibodies are well known in the art. Examples include ELISA, RIA, and fluorescent activated cell sorting (FACS). Such immunoassays typically involve the formation of complexes between the protein and its specific antibody and the measurement of such complexes. These and other assays are described in Pound (supra). The method may employ a two-site, monoclonal-based immunoassay utilizing monoclonal antibodies reactive to two non-interfering epitopes, or a competitive binding assay. (See, e.g., Coligan et al. (1997) Current Protocols in Immunology, Wiley-Interscience, New York N.Y.; Pound, supra)

Therapeutics

The cDNA molecules and fragments thereof can be used in gene therapy. cDNA molecules can be delivered ex vivo to target cells, such as cells of bone marrow. Once stable integration and transcription and or translation are confirmed, the bone marrow may be reintroduced into the subject. Expression of the protein encoded by the cDNA may correct a disease state associated with mutation of a normal sequence, reduction or loss of an endogenous target protein, or overepression of an endogenous or mutant protein. Alternatively, cDNA molecules may be delivered in vivo using vectors such as retrovirus, adenovirus, adeno-associated virus, herpes simplex virus, and bacterial plasmids. Non-viral methods of gene delivery include cationic liposomes, polylysine conjugates, artificial viral envelopes, and direct injection of DNA (Anderson (1998) Nature 392: 25-30; Dachs et al. (1997) Oncol Res 9:313-325; Chu et al. (1998) J Mol Med 76(3-4):184-192; Weiss et al. (1999) Cell Mol Life Sci 55(3):334-358; Agrawal (1996) Antisense Therapeutics, Humana Press, Totowa N.J.; and August et al. (1997) Gene Therapy (Advances in Pharmacology, Vol. 40), Academic Press, San Diego Calif.).

In addition, expression of a particular protein can be modulated through the specific binding of a fragment of a cDNA molecule to a genomic sequence or an mRNA molecule which encodes the protein or directs its transcription or translation. The cDNA molecule can be modified or derivatized to any RNA-like or DNA-like material including peptide nucleic acids, branched nucleic acids, and the like. These sequences can be produced biologically by transforming an appropriate host cell with an expression vector containing the sequence of interest.

Molecules which modulate the activity of the cDNA molecule or encoded protein are useful as therapeutics for brain disorders. Such molecules include agonists which increase the expression or activity of the polynucleotide or encoded protein, respectively; or antagonists which decrease expression or activity of the polynucleotide or encoded protein, respectively. In one aspect, an antibody which specifically binds the protein may be used directly as an antagonist or indirectly as a delivery mechanism for bringing a pharmaceutical agent to cells or tissues which express the protein.

Additionally, any of the proteins, or their ligands, or complementary nucleic acid sequences may be administered in combination with other appropriate therapeutic agents. Selection of the appropriate agents for use in combination therapy may be made by one of ordinary skill in the art, according to conventional pharmaceutical principles. The combination of therapeutic agents may act synergistically to affect the treatment or prevention of the conditions and disorders associated with an immune response. Using this approach, one may be able to achieve therapeutic efficacy with lower dosages of each agent, thus reducing the potential for adverse side effects. Further, the therapeutic agents may be combined with pharmaceutically-acceptable carriers including excipients and auxiliaries which facilitate processing of the active compounds into preparations which can be used pharmaceutically. Further details on techniques for formulation and administration may be found in the latest edition of Remington's Pharmaceutical Sciences (Maack Publishing, Easton Pa.).

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of underexpression or overexpression of genes of interest and for the development of methods for diagnosis and treatment of diseases. A mammal inbred to overexpress a particular gene (for example, secreted in milk) may also serve as a convenient source of the protein expressed by that gene.

Transgenic Animal Models

Transgenic rodents that overexpress or underexpress a gene of interest may be inbred and used to model human diseases or to test therapeutic or toxic agents. (See, e.g., U.S. Pat. Nos. 5,175,383 and 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells such as the mouse 129/SvJ cell line are placed in a blastocyst from the C57BL/6 mouse strain, they resume normal development and contribute to tissues of the live-born animal. ES cells are preferred for use in the creation of experimental knockout and knockin animals. The method for this process is well known in the art and the steps are: the cDNA is introduced into a vector, the vector is transformed into ES cells, transformed cells are identified and microinjected into mouse cell blastocysts, blastocysts are surgically transferred to pseudopregnant dams. The resulting chimeric progeny are genotyped and bred to produce heterozygous or homozygous strains.

Knockout Analysis

In gene knockout analysis, a region of a gene is enzymatically modified to include a non-natural intervening sequence such as the neomycin phosphotransferase gene (neo; Capecchi (1989) Science 244:1288-1292). The modified gene is transformed into cultured ES cells and integrates into the endogenous genome by homologous recombination. The inserted sequence disrupts transcription and translation of the endogenous gene.

Knockin Analysis

ES cells can be used to create knockin humanized animals or transgenic animal models of human diseases. With knockin technology, a region of a human gene is injected into animal ES cells, and the human sequence integrates into the animal cell genome. Transgenic progeny or inbred lines are studied and treated with potential pharmaceutical agents to obtain information on the progression and treatment of the analogous human condition.

As described herein, the uses of the cDNA molecules, provided in the Sequence Listing of this application, and their encoded proteins are exemplary of known techniques and are not intended to reflect any limitation on their use in any technique that would be known to the person of average skill in the art. Furthermore, the cDNA molecules provided in this application may be used in molecular biology techniques that have not yet been developed, provided the new techniques rely on properties of nucleotide sequences that are currently known to the person of ordinary skill in the art, e.g., the triplet genetic code, specific base pair interactions, and the like. Likewise, reference to a method may include combining more than one method for obtaining or assembling full length cDNA sequences that will be known to those skilled in the art. It is also to be understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

I. Preparation of cDNAs

Nucleic acid sequences (cDNA molecules) were made by RT-PCR from total cellular RNA using oligonucleotide primers corresponding to the 5' and 3' ends of the polynucleotides of SEQ ID NOs:1-50 (see Table 2). One primer was synthesized to initiate 5' extension of the known fragment, and the other, to initiate 3' extension of the known fragment. Cultured human neuroblastoma SHSY-5Y cells were obtained from American Type Culture Collection (accession no. CRL-2266) and were maintained in culture. The cells were lysed, total RNA was isolated using the RNA STAT-60 kit (Tel-Test, Friendswood Tex.). cDNA was amplified by PCR using Tay DNA polymerase with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified. The primer sequences are shown in Table 2

Two control cDNAs (GAPDH: SEQ ID NO:51; beta-actin: SEQ ID NO:52) were prepared in the same manner as the cDNAs of SEQ ID NOs:1-50, The GenBank Accession number is NM_002046 for GAPDH, and BC014861 for beta-actin.

Table 2 shows the identity of the genes from which the cDNA molecules were made, along with the sequence identifier for the gene, the GenBank accession number of the gene, the forward (5') and reverse (3') primers use to prepare the cDNA molecules corresponding to each gene, and the size of the product that results from the PCR reaction.

TABLE 2

```
SEQ ID NO:      1
Gene:           Homo sapiens, ATP synthase, H+ transporting, mitochondrial F0
                complex, subunit d, transcript variant 2, mRNA
GenBank #:      BC032245
Forward Primer: TCCTGGAATGAGACCCTCAC (SEQ ID NO: 53)
Reverse Primer: GAGACACCCACTCAGCACAA (SEQ ID NO: 54)
Product Size:   151 bp SEQ ID NO:      2
Gene:           Homo sapiens, ATP synthase, H+ transporting, mitochondrial F1
                complex, O subunit (oligomycin-sensitive conferring protein (OSCP)),
                mRNA
GenBank #:      BC021233
Forward Primer: GCTTGCTGAAAATGGTCGAT (SEQ ID NO: 55)
Reverse Primer: CGGATCAGTCTTAGCCTCCA (SEQ ID NO: 56)
Product Size:   205 bp SEQ ID NO:      3
Gene:           Homo sapiens, ATP synthase, H+ transporting, mitochondrial F0
                complex, subunit f, isoform 2, mRNA
GenBank #:      BC003678
Forward Primer: GCGGGACTTCAGTCCTAGTG (SEQ ID NO: 57)
Reverse Primer: CTCGTGCTTGAGATGCTTGT (SEQ ID NO: 58)
Product Size:   169 bp SEQ ID NO:      4
Gene:           Homo sapiens, Nuclear respiratory factor 1 (NRF1), mRNA
GenBank #:      NM_005011
Forward Primer: GATCGTCTTGTCTGGGGAAA (SEQ ID NO: 59)
Reverse Primer: GGTGACTGCGCTGTCTGATA (SEQ ID NO: 60)
Product Size:   244 bp
```

TABLE 2-continued

```
SEQ ID NO:      5
Gene:           Homo sapiens, mitochondrial DNA-encoded Cytochrome Oxidase
                Subunit I, mRNA
GenBank #:      NC_001807
Forward Primer: GGCCTGACTGGCATTGTATT (SEQ ID NO: 61)
Reverse Primer: TGGCGTAGGTTTGGTCTAGG (SEQ ID NO: 62)
Product Size:   178 bp SEQ ID NO:      6
Gene:           Homo sapiens, Interferon Gamma, mRNA
GenBank #:      X13274
Forward Primer: TTCAGCTCTGCATCGTTTTG (SEQ ID NO: 63)
Reverse Primer: TCTTTTGGATGCTCTGGTCA (SEQ ID NO: 64)
Product Size:   246 bp SEQ ID NO:      7
Gene:           Homo sapiens, Inositol (myo)-1(or 4)-monophosphatase 2, mRNA
GenBank #:      BC017176
Forward Primer: TCAAAGGCCTTGGTTCTGAC (SEQ ID NO: 65)
Reverse Primer: GTGCAGGCCAAACTGGTAAT (SEQ ID NO: 66)
Product Size:   189 bp SEQ ID NO:      8
Gene:           Human L-iditol-2 dehydrogenase (Sorbitol dehydrogenase), mRNA
GenBank #:      L29008
Forward Primer: CTCCCCGAGAAAATGATGAA (SEQ ID NO: 67)
Reverse Primer: CACAGAAAGTGGCTCGATCA (SEQ ID NO: 68)
Product Size:   188 bp SEQ ID NO:      9
Gene:           Homo sapiens, mitochondrial DNA-encoded Cytochrome Oxidase
                Subunit 11, mRNA
GenBank #:      NC_001807
Forward Primer: TTCATGATCACGCCCTCATA (SEQ ID NO: 69)
Reverse Primer: TAAAGGATGCGTAGGGATGG (SEQ ID NO: 70)
Product Size:   187 bp SEQ ID NO:      10
Gene:           Homo sapiens, Transcription factor A, mitochondrial (TEAM), mRNA
GenBank #:      NM_003201
Forward Primer: CCGAGGTGGTTTTCATCTGT (SEQ ID NO: 71)
Reverse Primer: TCCGCCCTATAAGCATCTTG (SEQ ID NO: 72)
Product Size:   203 bp SEQ ID NO:      11
Gene:           Homo sapiens, Glial Fibrillary Acidic Protein (GFAP), mRNA
GenBank #:      BC013596
Forward Primer: ACATCGAGATCGCCACCTAC (SEQ ID NO: 73)
Reverse Primer: ATCTCCACGGTCTTCACCAC (SEQ ID NO: 74)
Product Size:   166 bp SEQ ID NO:      12
Gene:           Homo sapiens, heat shock 60 kDa protein 1 (chaperonin), transcript
                variant 1, mRNA
GenBank #:      BC002676
Forward Primer: CATTCCAGCCTTGGACTCAT (SEQ ID NO: 75)
Reverse Primer: TCACAACCTTTGTTGGGTCA (SEQ ID NO: 76)
Product Size:   236 bp SEQ ID NO:      13
Gene:           Homo sapiens, Lactate dehydrogenase B (LDH-B), mRNA
GenBank #:      BT019765
Forward Primer: CCAACCCAGTGGACATTCTT (SEQ ID NO: 77)
Reverse Primer: AAACACCTGCCACATTCACA (SEQ ID NO: 78)
Product Size:   219 bp SEQ ID NO:      14
Gene:           Homo sapiens, Hexokinase 1 (HK1), mRNA
GenBank #:      M75126
Forward Primer: CCTGGGAGATTTCATGGAGA (SEQ ID NO: 79)
Reverse Primer: GTGCCCACTGTGTCATTCAC (SEQ ID NO: 80)
Product Size:   240 bp SEQ ID NO:      15
Gene:           Homo sapiens, Glycogen Synthase Kinase 3 beta, mRNA
GenBank #:      BC012760
Forward Primer: ATTACGGGACCCAAATGTCA (SEQ ID NO: 81)
Reverse Primer: TGCAGAAGCAGCATTATTGG (SEQ ID NO: 82)
Product Size:   217 bp
```

TABLE 2-continued

```
SEQ ID NO:       16
Gene:            Homo sapiens, ADP-ribosylation factor 4-like, mRNA
GenBank #:       BC000043
Forward Primer:  GACCACTGTGGCGCTCTTAT (SEQ ID NO: 83)
Reverse Primer:  CAGCCTCTTCTCCACCTCAG (SEQ ID NO: 84)
Product Size:    206 bp SEQ ID NO:       17
Gene:            Homo sapiens, Adrenomedullin precursor, mRNA
GenBank #:       D14874
Forward Primer:  CGTCGGAGTTTCGAAAGAAG (SEQ ID NO: 85)
Reverse Primer:  CCCTGGAAGTTGTTCATGCT (SEQ ID NO: 86)
Product Size:    206 bp SEQ ID NO:       18
Gene:            Homo sapiens, protein kinase C alpha (PKC alpha), mRNA
GenBank #:       X52479
Forward Primer:  GTGGCAAAGGAGCAGAGAAC (SEQ ID NO: 87)
Reverse Primer:  TGTAAGATGGGGTGCACAAA (SEQ ID NO: 88)
Product Size:    151 bp SEQ ID NO:       19
Gene:            Homo sapiens, protein kinase C, beta 1, transcript variant 2
                 (PKC beta 1), mRNA
GenBank #:       BC036472
Forward Primer:  TGAAGGGGAGGATGAAGATG (SEQ ID NO: 89)
Reverse Primer:  TAAGGGGGCTGGATCTCTTT (SEQ ID NO: 90)
Product Size:    228 bp SEQ ID NO:       20
Gene:            Homo sapiens, protein kinase C delta-type (PKC delta-type), mRNA
GenBank #:       D10495
Forward Primer:  CAACTACATGAGCCCCACCT (SEQ ID NO: 91)
Reverse Primer:  GAGGCTCTCTGGGTGACTTG (SEQ ID NO: 92)
Product Size:    189 bp SEQ ID NO:       21
Gene:            Homo sapiens, 80K-H protein (Protein Kinase C substrate), mRNA
GenBank #:       J03075
Forward Primer:  AACGGGGAGTTTGCTTACCT (SEQ ID NO: 93)
Reverse Primer:  CGTGCCTTGCTCATACTTCA (SEQ ID NO: 94)
Product Size:    195 bp
SEQ ID NO:       22

Gene:            Homo sapiens, Protein kinase C inhibitor-2, mRNA
GenBank #:       AF085236
Forward Primer:  TGAGGACCAGCAGTGTCTTG (SEQ ID NO: 95)
Reverse Primer:  CCATCGTTGATCACAAGTCG (SEQ ID NO: 96)
Product Size:    204 bp SEQ ID NO:       23
Gene:            Homo sapiens, Ca2+/calmodulin-dependent protein kinase kinase beta
                 (CAMKKB), mRNA
GenBank #:       AF140507
Forward Primer:  GCTGACTTTGGTGTGAGCAA (SEQ ID NO: 97)
Reverse Primer:  AATTCCAGGGCCTGACTCTT (SEQ ID NO: 98)
Product Size:    242 bp SEQ ID NO:       24
Gene:            Homo sapiens, heat shock protein (HSP 40), E. coli DnaJ homologue,
                 mRNA
GenBank #:       L08069
Forward Primer:  ATTGCCGAGGTACTGGAATG (SEQ ID NO: 99)
Reverse Primer:  GCCATCTTTCATGCCTTTGT (SEQ ID NO: 100)
Product Size:    203 bp SEQ ID NO:       25
Gene:            Homo sapiens, Transient Receptor Potential Cation Channel subfamily
                 C, member 7 (TRPC7), mRNA
GenBank #:       NM_020389
Forward Primer:  GTTAAAACCCTGCCAAACGA (SEQ ID NO: 101)
Reverse Primer:  GGACAGCATCCCGAAATCTA (SEQ ID NO: 102)
Product Size:    204 bp
```

TABLE 2-continued

```
SEQ ID NO:      26
Gene:           Homo sapiens, translocase of outer mitochondrial membrane homolog
                20 homolog (yeast) (TOM 20), mRNA
GenBank #:      BC000882
Forward Primer: AAACAGAAGCTTGCCAAGGA (SEQ ID NO: 103)
Reverse Primer: CATCTGGAACACTGGTGGTG (SEQ ID NO: 104)
Product Size:   234 bp SEQ ID NO:      27
Gene:           Homo sapiens, Interleukin-10 (IL-10), mRNA
GenBank #:      M57627
Forward Primer: TGCCTTCAGCAGAGTGAAGA (SEQ ID NO: 105)
Reverse Primer: GGTCTTGGTTCTCAGCTTGG (SEQ ID NO: 106)
Product Size:   170 bp SEQ ID NO:      28
Gene:           Homo sapiens, Interleukin 2 receptor (IL-2R), mRNA
GenBank #:      X01057
Forward Primer: ATCAGTGCGTCCAGGGATAC (SEQ ID NO: 107)
Reverse Primer: GACGAGGCAGGAAGTCTCAC (SEQ ID NO: 108)
Product Size:   197 bp SEQ ID NO:      29
Gene:           Homo sapiens, Proteasome (prosome, macropain) 26S subunit,
                ATPase, 6 mRNA
GenBank #:      BT006843
Forward Primer: GCTGCGTCCAGGAAGATTAG (SEQ ID NO: 109)
Reverse Primer: TGCGAACATACCTGCTTCAG (SEQ ID NO: 110)
Product Size:   196 bp SEQ ID NO:      30
Gene:           Homo sapiens, Calbindin 1, 28 kDa (CALB1), mRNA
GenBank #:      NM_004929
Forward Primer: ATCCCTCATCACAGCCTCAC (SEQ ID NO: 111)
Reverse Primer: TGCCCATACTGATCCACAAA (SEQ ID NO: 112)
Product Size:   177 bp SEQ ID NO:      31
Gene:           Homo sapiens, heat shock 70 kDa protein 5 (Glucose-regulated Protein
                78 kDa) (GRP 78), mRNA
GenBank #:      BC020235
Forward Primer: TAGCGTATGGTGCTGCTGTC (SEQ ID NO: 113)
Reverse Primer: TTTGTCAGGGGTCTTTCACC (SEQ ID NO: 114)
Product Size:   241 bp SEQ ID NO:      32
Gene:           Homo sapiens, (HepG2) glucose transporter gene, mRNA
GenBank #:      K03195
Forward Primer: CTTCACTGTCGTGTCGCTGT (SEQ ID NO: 115)
Reverse Primer: TGAAGAGTTCAGCCACGATG (SEQ ID NO: 116)
Product Size:   230 bp SEQ ID NO:      33
Gene:           Homo sapiens, solute carrier family 2 (facilitated glucose
                transporter), member 3, mRNA
GenBank #:      BC039196
Forward Primer: ACCGGCTTCCTCATTACCTT (SEQ ID NO: 117)
Reverse Primer: AGGCTCGATGCTGTTCATCT (SEQ ID NO: 118)
Product Size:   159 bp SEQ ID NO:      34
Gene:           Homo sapiens, B-cell lymphoma 3-encoded protein (bcl-3) mRNA
GenBank #:      M31732
Forward Primer: CCCTATACCCCATGATGTGC (SEQ ID NO: 119)
Reverse Primer: GGTGTCTGCCGTAGGTTGTT (SEQ ID NO: 120)
Product Size:   199 bp SEQ ID NO:      35
Gene:           Homo sapiens, Liver-type 1-phosphofructokinase (PFKL), mRNA
GenBank #:      X15573
Forward Primer: GGAGCTTCGAGAACAACTGG (SEQ ID NO: 121)
Reverse Primer: CTGTGTGTCCATGGGAGATG (SEQ ID NO: 122)
Product Size:   168 bp SEQ ID NO:      36
Gene:           Homo sapiens, translocation (11;19) fusion protein (E2A/PRL), mRNA
GenBank #:      M31522
Forward Primer: CAAGCTAACTCGCCCTCAAC (SEQ ID NO: 123)
Reverse Primer: GCTGCGAGTCCATCACTGTA (SEQ ID NO: 124)
Product Size:   206 bp
```

TABLE 2-continued

```
SEQ ID NO:      37
Gene:           Homo sapiens, Hexose-6-phosphate dehydrogenase (glucose 1-
                dehydrogenase) (H6PD)
GenBank #:      NM_004285
Forward Primer: GCACAAGCTTCAGGTCTTCC (SEQ ID NO: 125)
Reverse Primer: GAACAAGATCCGAGCGTAGC (SEQ ID NO: 126)
Product Size:   247 bp SEQ ID NO:      38
Gene:           Homo sapiens, ATPase, Na+30/K+transporting, alpha 2 (+30) polypep-
                tide,
                mRNA
GenBank #:      BC052271
Forward Primer: CGCAAATACCAAGTGGACCT (SEQ ID NO: 127)
Reverse Primer: AAGCAGAGGATAGCCCCAAT (SEQ ID NO: 128)
Product Size:   179 bp SEQ ID NO:      39
Gene:           Homo sapiens, ATPase, Na+30/K+transporting, alpha 3 polypeptide
                (ATP1A3), mRNA
GenBank #:      NM_152296
Forward Primer: CTGTCAGAGACAGGGTGCAA (SEQ ID NO: 129)
Reverse Primer: ATTGCTGGTCAGGGTGTAGG (SEQ ID NO: 130)
Product Size:   238 bp SEQ ID NO:      40
Gene:           Homo sapiens, Phospholipase C, gamma 2 (phosphatidylinositol-
                specific), mRNA
GenBank #:      BC007565
Forward Primer: AACCAACCAGCAAAACCAAG (SEQ ID NO: 131)
Reverse Primer: TTTGTCCCTTTGGGTAGACG (SEQ ID NO: 132)
Product Size:   159 bp SEQ ID NO:      41
Gene:           Homo sapiens, aldo-keto reductase family 1, member B1 (aldose
                reductase)
GenBank #:      BC010391
Forward Primer: TGCCACCCATATCTCACTCA (SEQ ID NO: 133)
Reverse Primer: TGTCACAGACTTGGGGATCA (SEQ ID NO: 134)
Product Size:   240 bp SEQ ID NO:      42
Gene:           Homo sapiens, mitochondrial DNA-encoded Cytochrome Oxidase
                Subunit III, mRNA
GenBank #:      NC_001807
Forward Primer: CCCGCTAAATCCCCTAGAAG (SEQ ID NO: 135)
Reverse Primer: GGAAGCCTGTGGCTACAAAA (SEQ ID NO: 136)
Product Size:   245 bp SEQ ID NO:      43
Gene:           Homo sapiens, Cytochrome c Oxidase COX Subunit IV (COX IV),
                mRNA
GenBank #:      M21575
Forward Primer: GGCACTGAAGGAGAAGGAGA (SEQ ID NO: 137)
Reverse Primer: GGGCCGTACACATAGTGCTT (SEQ ID NO: 138)
Product Size:   204 bp SEQ ID NO:      44
Gene:           Homo sapiens. Cytochrome c Oxidase Subunit Va (COX5A), nuclear
                gene encoding mitochondrial protein, mRNA
GenBank #:      NM_004255
Forward Primer: GCATGCAGACGGTTAAATGA (SEQ ID NO: 139)
Reverse Primer: AGTTCCTCCGGAGTGGAGAT (SEQ ID NO: 140)
Product Size:   152 bp SEQ ID NO:      45
Gene:           Homo sapiens, Cytochrome c Oxidase Subunit Vb (COX5B), mRNA
GenBank #:      NM_001862
Forward Primer: ACTGGGTTGGAGAGGGAGAT (SEQ ID NO: 141)
Reverse Primer: AGACGACGCTGGTATTGTCC (SEQ ID NO: 142)
Product Size:   172 bp SEQ ID NO:      46
Gene:           Homo sapiens. High-mobility group box 1 (HMGB1), mRNA
GenBank #:      NM_002128
Forward Primer: ATATGGCAAAAGCGGACAAG (SEQ ID NO: 143)
Reverse Primer: GCAACATCACCAATGGACAG (SEQ ID NO: 144)
Product Size:   193 bp
```

TABLE 2-continued

```
SEQ ID NO:       47
Gene:            Homo sapiens, Amyloid Precursor homologue, mRNA
GenBank #:       L09209
Forward Primer:  TTCCAAGCCATGGTTAAAGC (SEQ ID NO: 145)
Reverse Primer:  GCCAACACATGCTGGTAATG (SEQ ID NO: 146)
Product Size:    248 bp SEQ ID NO:       48
Gene:            Homo sapiens, Adrenergic alpha-1b receptor protein, mRNA
GenBank #:       U03865
Forward Primer:  CCTGAGGATCCATTCCAAGA (SEQ ID NO: 147)
Reverse Primer:  CGGTAGAGCGATGAAGAAGG (SEQ ID NO: 148)
Product Size:    190 bp SEQ ID NO:       49
Gene:            Homo sapiens, Complement Component 1, r subcomponent (C1R), mRNA
GenBank #:       NM_001733
Forward Primer:  ATAGAGGGGAACCAGGTGCT (SEQ ID NO: 149)
Reverse Primer:  TACGGGCCTTGTAGGTGTTC (SEQ ID NO: 150)
Product Size:    172 bp SEQ ID NO:       50
Gene:            Homo sapiens, Endoglin, mRNA 3' end
GenBank #:       J05481
Forward Primer:  CACTAGCCAGGTCTCGAAGG (SEQ ID NO: 151)
Reverse Primer:  CTGAGGACCAGAAGCACCTC (SEQ ID NO: 152)
Product Size:    165 bp SEQ ID NO:       51
Gene:            Homo sapiens, Glyceraldehyde 3 phosphate dehydrogenase (GAPDH),
                 triRNA
GenBank #:       NM_002046
Forward Primer:  GAGTCAACGGATTTGGTCGT (SEQ ID NO: 153)
Reverse Primer:  TTGATTTTGGAGGGATCTCG (SEQ ID NO: 154)
Product Size:    238 bp SEQ ID NO:       52
Gene:            Homo sapiens, Beta actin, mRNA
GenBank #:       BC014861
Forward Primer:  GGACTTCGAGCAAGAGATGG (SEQ ID NO: 155)
Reverse Primer:  AGCACTGTGTTGGCGTACAG (SEQ ID NO: 156)
Product Size:    234 bp
```

II. Selection of Sequences, Dot-Blot and Use

Purified cDNA molecules corresponding to SEQ ID NOs: 1-50 and the GAPDH and beta-actin controls were immobilized on nylon membranes by applying 10 ul of each particular cDNA at an average concentration of 10 ng/ul to the membrane. The membranes were UV-crosslinked using a STRATALINKER UV-crosslinker (Stratagene), and baked at 120° C. for 30 min to form the arrays further used as described herein. Thirty dot-blot membranes (arrays) were used to evaluate differential expression across the patient and control samples. Each of the 30 membranes had one location corresponding to each of the 50 different purified cDNA molecules and the controls. Thus, each membrane had 52 different cDNA molecules arranged on its surface.

III. Preparation of Samples

Test samples were prepared from samples obtained from the 25 subjects shown in Table 3 for hybridization to the arrays. Total RNA was extracted from the samples using the RNA STAT-60 kit (Tel-Test, Friendswood Tex.). Each RNA sample was reverse transcribed using MMLV reverse-transcriptase, 0.05 pg/ul oligo-d(T) primer (21 mer), 1× first strand buffer, 0.03 units/ul RNase inhibitor, 500 uM dATP, 500 uM dGTP, 500 uM dTTP, 40 uM dCTP, and 40 uM $^{32}$P-dCTP. The reverse transcription reaction was performed in a 30 ul volume containing 200 ng RNA using the SUPERSCRIPT III kit (Invitrogen, Carlsbad. Calif.). Reactions were incubated at 45° C. for 1 hr, treated with 1 ul of DNase-free RNaseA and incubated for 10 minutes at 60° C. to the stop the reaction and degrade the RNA. cDNA molecules were purified using two successive gel filtration spin columns (Qiagen) to form the test samples further used as described herein.

Table 3 contains information about the patients from which blood samples used in the preparation of nucleic acids for hybridization with the arrays were obtained. Column 2 shows the illness, column 3 shows the patient ID #, columns 4 shows the gender and column 5 shows the age, and column 6 shows the ethnicity of the donor. Blood sample were obtained from practicing psychiatrists within the Columbia, Md. area by a qualified phlebotomist and with the consent of patients. Samples were comprised of whole blood, from which RNA was isolated.

TABLE 3

| SAMPLE NO. | ILLNESS | PATIENT ID | GENDER | AGE | ETHNICITY |
|---|---|---|---|---|---|
| 1 | Normal | CT20 | male | | Caucasian |
| 2 | | CT27 | male | | Asian |
| 3 | | CT28 | male | | Caucasian |
| 4 | | CT1 | male | 45 | Asian |
| 5 | | CT2 | male | 69 | Asian |
| 6 | Bipolar I | CT3 | female | | Caucasian |
| 7 | | CT5 | male | | Caucasian |
| 8 | | 1035 | female | 53 | Caucasian |
| 9 | | 1048 | female | 42 | Caucasian |
| 10 | | 1050 | female | 30 | Caucasian |
| 11 | | 1053 | female | 14 | Hispanic |
| 12 | | 1054 | male | 16 | Hispanic |

TABLE 3-continued

| SAMPLE NO. | ILLNESS | PATIENT ID | GENDER | AGE | ETHNICITY |
|---|---|---|---|---|---|
| 13 | | 1057 | female | 46 | Caucasian |
| 14 | ADHD | 1061 | female | 34 | Caucasian |
| 15 | | 1062 | female | 23 | Caucasian |
| 16 | | 1075 | male | 16 | Caucasian |
| 17 | | 1076 | female | 48 | Caucasian |
| 18 | Unipolar | CT15 | male | | Caucasian |
| 19 | | CT29 | female | | Black |
| 20 | | 1002 | male | 28 | Caucasian |
| 21 | | 1077 | female | 26 | Caucasian |
| 22 | Schizophrenia | CT11 | male | | Black |
| 23 | | CT16 | male | | Black |
| 24 | | NA36 | male | 35 | Caucasian |
| 25 | | NA37 | male | 40 | Caucasian |

IV. Hybridization and Detection

For each of the 25 different test samples prepared in section III, above, 30 ul of test sample containing 0.2 ug of the $^{32}$P-labeled cDNA was added to 5 ml of hybridization solution (NorthemsMax, Ambion). Each of the 25 resulting solutions were added to one of the blots produced in section II. above, and the blots were hybridized at 37° C. for 24 hr. The blots were washed twice for 10 min at 45° C. in low stringency wash buffer (1×SSC, 0.1% SDS), once for 15 min at 55° C., once at 45° C. in high stringency wash buffer (0.1×SSC), and dried.

Reporter-labeled hybridization complexes were detected by exposing the blot to x-ray film and developing the film after different periods of exposure. The intensity of hybridization was quantified by the signal intensity of the hybridized band using a densitometer.

The results of the gene expression analysis of eight different genes are shown in FIGS. 1-8. The intensity of hybridization was determined using a densitometer for each of the eight selected genes on each of the 25 blots. The ratio of hybridization intensity of the test gene to that of the control gene (beta-actin) was determined. The ratio was plotted and is shown in the FIGS. 1-8. Table 4 shows the results obtained from each of the eight genes analyzed.

TABLE 4

| TYPE OF ILLNESS | GENE | ACCESSION # | CHANGE IN GENE EXPRESSION |
|---|---|---|---|
| Bipolar I Disorder | F0D | BC032245 | downregulated |
| | OSCP | BC021233 | downregulated |
| | F0F | BC003678 | downregulated |
| | NRF-1 | NM_005011 | downregulated |
| | COX I | NC_001807 | downregulated |
| | IFN Gamma | X13274 | no significant difference |
| | IMPase | BC017176 | no significant difference |
| | SDH | L29008 | no significant difference |
| ADHD | F0D | BC032245 | no significant difference |
| | OSCP | BC021233 | downregulated |
| | F0F | BC003678 | no significant difference |
| | NRF-1 | NM_005011 | downregulated |
| | COX I | NC_001807 | downregulated |
| | IFN Gamma | X13274 | downregulated |
| | IMPase | BC017176 | upregulated |
| | SDH | L29008 | no significant difference |
| Unipolar | F0D | BC032245 | upregulated |
| | OSCP | BC021233 | no significant difference |
| | F0F | BC003678 | upregulated |
| | NRF-1 | NM_005011 | downregulated |
| | COX I | NC_001807 | downregulated |
| | IFN Gamma | X13274 | downregulated |
| | IMPase | BC017176 | upregulated |
| | SDH | L29008 | upregulated |
| Schizophrenia | F0D | BC032245 | downregulated |
| | OSCP | BC021233 | downregulated |
| | F0F | BC003678 | downregulated |
| | NRF-1 | NM_005011 | no significant difference |
| | COX I | NC_001807 | no significant difference |
| | IFN Gamma | X13274 | no significant difference |
| | IMPase | BC017176 | upregulated |
| | SDH | L29008 | no significant difference |

V. Other Hybridization Technologies and Analyses

Other hybridization technologies utilize a variety of substrates such as DNA array, capillary tubes, etc. Arranging cDNA molecules on polymer coated slides is described as follows.

The cDNA molecules are applied to a membrane substrate by one of the following methods. A mixture of cDNA molecules is fractionated by gel electrophoresis and transferred to a nylon membrane by capillary transfer. Alternatively, the cDNA molecules are individually ligated to a vector and inserted into bacterial host cells to form a library. The cDNA molecules are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37° C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNA molecules are amplified from bacterial vectors by thirty cycles of PCR using primers complementary to vector sequences flanking the insert. PCR amplification increases a starting concentration of 1-2 ng nucleic acid to a final quantity greater than 5 μg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above.

Hybridization probes derived from cDNA molecules of the Sequence Listing are employed for screening cDNA molecules, mRNA molecules, or genomic DNA in membrane-based hybridizations. Probes are prepared by diluting the cDNA molecules to a concentration of 40-50 ng in 45 μl TE buffer, denaturing by heating to 100° C. for five min, and briefly centrifuging. The denatured cDNA is then added to a REDIPRIME tube (APB), gently mixed until blue color is evenly distributed, and briefly centrifuged. Five microliters of $^{32}$P-dCTP is added to the tube, and the contents are incubated at 37° C. for 10 min. The labeling reaction is stopped by adding 5 μl of 0.2 M EDTA, and probe is purified from unincorporated nucleotides using a PROBEQUANT G-50 microcolumn (APB). The purified probe is heated to 100° C. for five min., snap cooled for two min. on ice.

Membranes are pre-hybridized in hybridization solution containing 1% Sarkosyl and 1× high phosphate buffer (0.5 M NaCl, 0.1 M Na2HPO$_4$, 5 mM EDTA, pH 7) at 55° C. for two hr. The probe, diluted in 15 ml fresh hybridization solution, is then added to the membrane. The membrane is hybridized with the probe at 55° C. for 16 hr. Following hybridization, the membrane is washed for 15 min at 25° C. in 1 mM Tris (pH 8.0), 1% Sarkosyl, and four times for 15 min each at 25° C. in 1 mM Tris (pH 8.0). To detect hybridization complexes, XOMAT-AR film (Eastman Kodak, Rochester N.Y.) is exposed to the membrane overnight at −70° C., developed, and examined.

VI. Production of Specific Antibodies

A denatured protein from a reverse phase HPLC separation is obtained in quantities up to 75 mg. This denatured protein is used to immunize mice or rabbits following standard protocols. About 100 μg is used to immunize a mouse, while up to 1 mg is used to immunize a rabbit. The denatured protein is radioiodinated and incubated with murine B-cell hybridomas to screen for monoclonal antibodies. About 20 mg of protein is sufficient for labeling and screening several thousand clones.

In another approach, the amino acid sequence translated from a cDNA of the invention is analyzed using PROTEAN software (DNASTAR) to determine regions of high immunogenicity, antigenically-effective portions of the protein. The optimal sequences for immunization are usually at the C-terminus, the N-terminus, and those intervening, hydrophilic regions of the protein that are likely to be exposed to the external environment when the protein is in its natural conformation. Typically, oligopeptides about 15 residues in length are synthesized using an ABI 431 Peptide synthesizer (PE Biosystems) using Fmoc-chemistry and then coupled to keyhole limpet hemocyanin (KLH; Sigma Aldrich) by reaction with M-maleimidobenzoyl-N-hydroxysuccinimide ester. If necessary, a cysteine may be introduced at the N-terminus of the peptide to permit coupling to KLH. Rabbits are immunized with the oligopeptide-KLH complex in complete Freund's adjuvant. The resulting antisera are tested for antipeptide activity by binding the peptide to plastic, blocking with 1% BSA, reacting with rabbit antisera, washing, and reacting with radioiodinated goat anti-rabbit IgG.

Hybridomas are prepared and screened using standard techniques. Hybridomas of interest are detected by screening with radioiodinated protein to identify those fusions producing a monoclonal antibody specific for the protein. In a typical protocol, wells of 96 well plates (FAST, Becton-Dickinson, Palo Alto Calif.) are coated with affinity-purified, specific rabbit-anti-mouse (or suitable anti-species Ig) antibodies at 10 mg/ml. The coated wells are blocked with 1% BSA and washed and exposed to supernatants from hybridomas. After incubation, the wells are exposed to radiolabeled protein at 1 mg/mi. Clones producing antibodies bind a quantity of labeled protein that is detectable above background.

Such clones are expanded and subjected to 2 cycles of cloning at 1 cell/3 wells. Cloned hybridomas are injected into pristane-treated mice to produce ascites, and monoclonal antibody is purified from the ascitic fluid by affinity chromatography on protein A (APB). Monoclonal antibodies with affinities of at least $10^8$ $M^{-1}$, preferably $10^9$ to $10^{10}$ M or stronger, are made by procedures well known in the art.

VII. Screening Molecules for Specific Binding with the CDNA or Protein

The cDNA or fragments thereof and the protein or portions thereof are labeled with $^{32}$P-cICTP, Cy3-dCTP, Cy5-dCTP (APB), or BIODIPY or FITC (Molecular Probes), respectively. Candidate molecules or compounds previously arranged on a substrate are incubated in the presence of labeled nucleic or amino acid. After incubation under conditions for either a cDNA or a protein, the substrate is washed, and any position on the substrate retaining label, which indicates specific binding or complex formation, is assayed. The binding molecule is identified by its arrayed position on the substrate. Data obtained using different concentrations of the nucleic acid or protein are used to calculate affinity between the labeled nucleic acid or protein and the bound molecule. High throughput screening using very small assay volumes and very small amounts of test compound is fully described in Burbaum et al. U.S. Pat. No. 5,876,946.

All patents and publications mentioned in the specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. A composition comprising a plurality of cDNA molecules, wherein the plurality of cDNA molecules consists of two or more cDNA molecules selected from the group consisting of SEQ ID NOs:1-50, wherein one or more of SEQ ID NOs:1-50 may be substituted for by the complement of said cDNA molecule.

2. The composition of claim 1, wherein said plurality of cDNA molecules consists of SEQ ID NOs:1-8, wherein one or more of SEQ ID NOs:1-8 may be substituted for by the complement of said cDNA molecule.

3. A composition comprising a plurality of cDNA molecules, wherein the plurality of cDNA molecules consists of SEQ ID NOs:1-15, wherein one or more of SEQ ID NOs: 1-15 may be substituted for by the complement of said cDNA molecule.

4. The composition of claim 1 or 3, wherein the cDNA molecules are immobilized on a substrate.

5. The composition of claim 4, wherein the substrate is selected from the group consisting of a nylon membrane, a nitrocellulose membrane, a polypropylene support, a glass support and a silicon support.

6. An array comprising a plurality of cDNA molecules immobilized on a substrate, wherein the plurality of cDNA molecules consists of two or more cDNA molecules selected from the group consisting of SEQ ID NOs:1-50, wherein one or more of SEQ ID NOs:1-50 may be substituted for by the complement of said cDNA molecule.

7. The array of claim 6, wherein said plurality of cDNA molecules consists of SEQ ID NOs:1-8, wherein one or more of SEQ ID NOs:1-8 may be substituted for by the complement of said cDNA molecule.

8. An array comprising a plurality of cDNA molecules immobilized on a substrate, wherein the plurality of cDNA molecules consists of SEQ ID NOs:1-15, wherein one or more of SEQ ID NOs:1-15 may be substituted for by the complement of said cDNA molecule.

9. The array of claim 6 or 8, wherein the substrate is selected from the group consisting of a nylon membrane, a nitrocellulose membrane, a polypropylene support, a glass support and a silicon support.

10. A high throughput method for detecting differential expression of one or more cDNA molecules in a sample containing nucleic acids, the method comprising:
(a) hybridizing the array of claim 6 with nucleic acids of the sample, thereby forming one or more hybridization complexes;
(b) detecting the hybridization complexes; and
(c) comparing the hybridization complexes with those of a standard, wherein differences in the size and intensity of each hybridization complex indicates differential expression of cDNAs in the sample.

11. The method of claim 10, wherein the sample is blood or is obtained by separation from blood.

12. The method of claim 10 wherein the nucleic acids are amplified prior to hybridization.

13. A high throughput method of screening a library of molecules or compounds to identify a ligand which specifically binds a cDNA molecule, the method comprising:
(a) combining the composition of claim 1 with the library of molecules or compounds under conditions to allow specific binding; and
(b) detecting specific binding between each cDNA molecule and at least one molecule or compound, thereby identifying a ligand that specifically binds to each cDNA molecule.

14. The method of claim 13 wherein the library is selected from the group consisting of DNA molecules, RNA molecules, mimetics, peptides, peptide nucleic acids, proteins, and transcription factors.

15. A high throughput method for detecting differential expression of one or more cDNA molecules in a sample containing nucleic acids, the method comprising:
(a) hybridizing the array of claim 8 with nucleic acids of the sample, thereby forming one or more hybridization complexes;
(b) detecting the hybridization complexes; and
(c) comparing the hybridization complexes with those of a standard, wherein differences in the size and intensity of each hybridization complex indicates differential expression of cDNAs in the sample.

16. The method of claim 15 wherein the nucleic acids are amplified prior to hybridization.

17. The method of claim 15, wherein the sample is blood or is obtained by separation from blood.

18. A high throughput method of screening a library of molecules or compounds to identify a ligand which specifically binds a cDNA molecule, the method comprising:
(a) combining the composition of claim 3 with the library of molecules or compounds under conditions to allow specific binding; and
(b) detecting specific binding between each cDNA molecule and at least one molecule or compound, thereby identifying a ligand that specifically binds to each cDNA molecule.

19. The method of claim 18 wherein the library is selected from the group consisting of DNA molecules, RNA molecules, mimetics, peptides, peptide nucleic acids, proteins, and transcription factors.

20. A high throughput method for detecting differential expression of two or more cDNA molecules in a sample containing nucleic acids, the method comprising:
(a) combining the composition of claim 1 with nucleic acids of the sample, forming one or more hybridization complexes; and
(b) detecting the hybridization complexes; and
(c) comparing the hybridization complexes with those of a standard, wherein differences in the size and intensity of each hybridization complex indicates differential expression of cDNAs in the sample.

21. The high throughput method of claim 20, wherein the two or more cDNA molecules are differentially expressed in a sample from a subject with a mental illness in comparison with a standard from a subject without a mental illness.

22. The high throughput method of claim 21, wherein said differential expression is a downregulation of at least two-fold in said sample from said subject with a mental illness.

23. The high throughput method of claim 21, wherein the mental illnesses is selected from the group consisting of bipolar I disorder, bipolar II disorder, unipolar disorder, schizophrenia, an attention deficit hyperactive disorder, an obsessive compulsive disorder, an anxiety disorder and a mood related disorder.

\* \* \* \* \*

SEQUENCE LISTING

```
<160> NUMBER OF SEQ ID NOS: 156

<210> SEQ ID NO 1
<211> LENGTH: 151
<212> TYPE: DNA
<213> ORGANISM: Homo sapiens

<400> SEQUENCE: 1
tcctggaatg agaccctcac ctccaggttg gctgctttac ctgagaatcc accagctatc      60
gactgggctt actacaaggc caatgtgcc aaggctggct tggtggatga ctttgagaag      120
aaggtgaaat cttgtgctga gtgggtgtct c                                    151

<210> SEQ ID NO 2
<211> LENGTH: 205
<212> TYPE: DNA
<213> ORGANISM: Homo sapiens
```

<400> SEQUENCE: 2

```
gcttgctgaa aatggtcgat taagcaatac ccaaggagtc gtttctgcct tttctaccat      60
gatgagtgtc catcgcggag aggtaccttg cacagtgacc tctgcatctc ctttagaaga     120
agccacactc tctgaattaa aaactgtcct caagagcttc ctaagtcaag gccaagtatt     180
gaaattggag gctaagactg atccg                                           205
```

<210> SEQ ID NO 3
<211> LENGTH: 169
<212> TYPE: DNA
<213> ORGANISM: Homo sapiens

<400> SEQUENCE: 3

```
gcgggacttc agtcctagtg gcattttcgg agcgtttcaa agaggttact accggtacta      60
caacaagtac atcaatgtga agaaggggag catctcgggg attaccatgg tgctggcatg     120
ctacgtgctc tttagctact ccttttccta caagcatctc aagcacgag                169
```

<210> SEQ ID NO 4
<211> LENGTH: 244
<212> TYPE: DNA
<213> ORGANISM: Homo sapiens

<400> SEQUENCE: 4

```
gatcgtcttg tctggggaaa ccgcagcagc cgtcggagca cttactggag tccaagatgc      60
taatggcctc tttatggcag atcgtgcagg tcgcaagtgg atcctgactg acaaagccac     120
aggcctggtc cagatccctg tgagcatgta ccagactgtg gtgaccagcc tcgcccaggg     180
caacggacca gtgcaggtgg ccatggcccc tgtgaccacc aggatatcag acagcgcagt     240
cacc                                                                  244
```

<210> SEQ ID NO 5
<211> LENGTH: 185
<212> TYPE: DNA
<213> ORGANISM: Homo sapiens

<400> SEQUENCE: 5

```
ggcctgactg gcattgtatt agcaaactca tcactagaca tcgtactaca cgacacgtac      60
tacgttgtag ctcacttcca ctatgtccta tcaataggag ctgtatttgc catcatagga     120
ggcttcattc actgatttcc cctattctca ggctacaccc tagaccaaac ctacgccaaa     180
atcca                                                                 185
```

<210> SEQ ID NO 6
<211> LENGTH: 246
<212> TYPE: DNA
<213> ORGANISM: Homo sapiens

<400> SEQUENCE: 6

```
ttcagctctg catcgttttg ggttctcttg gctgttactg ccaggaccca tatgtaaaag      60
aagcagaaaa ccttaagaaa tattttaatg caggtcattc agatgtagcg gataatggaa     120
ctcttttctt aggcatttg aagaattgga agaggagag tgacagaaaa ataatgcaga      180
gccaaattgt ctccttttac ttcaaacttt ttaaaaactt taaagatgac cagagcatcc     240
aaaaga                                                                246
```

```
<210> SEQ ID NO 7
<211> LENGTH: 189
<212> TYPE: DNA
<213> ORGANISM: Homo sapiens

<400> SEQUENCE: 7
tcaaaggcct tggttctgac agaaattggc cccaaacgtg accctgcgac cctgaagctg      60
ttcctgagta acatggagcg gctgctgcat gccaaggcgc atggggtccg agtgattgga     120
agctccacat tggcactctg ccacctggcc tcaggggccg cggatgccta ttaccagttt     180
ggcctgcac                                                             189

<210> SEQ ID NO 8
<211> LENGTH: 188
<212> TYPE: DNA
<213> ORGANISM: Homo sapiens

<400> SEQUENCE: 8
ctccccgaga aaatgatgaa ttctgcaaga tgggccgata caatctgtca ccttccatct      60
tcttctgtgc cacgcccccc gatgacggga acctctgccg gttctataag cacaatgcag     120
ccttttgtta caagcttcct gacaatgtca cctttgagga aggcgccctg atcgagccac     180
tttctgtg                                                              188

<210> SEQ ID NO 9
<211> LENGTH: 187
<212> TYPE: DNA
<213> ORGANISM: Homo sapiens

<400> SEQUENCE: 9
ttcatgatca cgccctcata atcatttttcc ttatctgctt cctagtcctg tatgcccttt      60
tcctaacact cacaacaaaa ctaactaata ctaacatctc agacgctcag gaaatagaaa     120
ccgtctgaac tatcctgccc gccatcatcc tagtcctcat cgccctccca tccctacgca     180
tccttta                                                               187

<210> SEQ ID NO 10
<211> LENGTH: 203
<212> TYPE: DNA
<213> ORGANISM: Homo sapiens

<400> SEQUENCE: 10
ccgaggtggt tttcatctgt cttggcaagt tgtccaaaga aacctgtaag ttcttaccct      60
cgatttctta aagaacaact acccatattt aaagctcaga acccagatgc aaaaactaca     120
gaactaatta aagaattgcc cagcgttgg agggaacttc ctgattcaaa gaaaaaaata     180
tatcaagatg cttatagggc gga                                             203

<210> SEQ ID NO 11
<211> LENGTH: 166
<212> TYPE: DNA
<213> ORGANISM: Homo sapiens

<400> SEQUENCE: 11
acatcgagat cgccacctac aggaagctgc tagagggcga ggagaaccgg atcaccattc      60
ccgtgcagac cttctccaac ctgcagattc gagaaaccag cctggacacc aagtctgtgt     120
cagaaggcca cctcaagagg aacatcgtgg tgaagaccgt ggagat                    166
```

```
<210> SEQ ID NO 12
<211> LENGTH: 236
<212> TYPE: DNA
<213> ORGANISM: Homo sapiens

<400> SEQUENCE: 12
cattccagcc ttggactcat tgactccagc taatgaagat caaaaaattg gtatagaaat       60
tattaaaaga acactcaaaa ttccagcaat gaccattgct aagaatgcag gtgttgaagg      120
atctttgata gttgagaaaa ttatgcaaag ttcctcagaa gttggttatg atgctatggc      180
tggagatttt gtgaatatgg tggaaaaagg aatcattgac ccaacaaagg ttgtga          236

<210> SEQ ID NO 13
<211> LENGTH: 219
<212> TYPE: DNA
<213> ORGANISM: Homo sapiens

<400> SEQUENCE: 13
ccaacccagt ggacattctt acgtatgtta cctggaaact aagtggatta cccaaacacc       60
gcgtgattgg aagtggatgt aatctggatt ctgctagatt tcgctacctt atggctgaaa      120
aacttggcat tcatcccagc agctgccatg gatggatttt ggggaacat ggcgactcaa       180 gtgtggctgt gtggagtggt gtgaatgtgg caggtgttt                              219

<210> SEQ ID NO 14
<211> LENGTH: 240
<212> TYPE: DNA
<213> ORGANISM: Homo sapiens

<400> SEQUENCE: 14
cctgggagat ttcatggaga aaaggaagat caaggacaag aagttacctg tgggattcac       60
gttttctttt ccttgccaac aatccaaaat agatgaggcc atcctgatca cctggacaaa      120
gcgatttaaa gcgagcggag tggaaggagc agatgtggtc aaactgctta acaaagccat      180
caaaaagcga ggggactatg atgccaacat cgtagctgtg gtgaatgaca cagtgggcac      240

<210> SEQ ID NO 15
<211> LENGTH: 217
<212> TYPE: DNA
<213> ORGANISM: Homo sapiens

<400> SEQUENCE: 15
attacgggac ccaaatgtca aactaccaaa tgggcgagac acacctgcac tcttcaactt       60
caccactcaa gaactgtcaa gtaatccacc tctggctacc atccttattc ctcctcatgc      120
tcggattcaa gcagctgctt caaccccac aaatgccaca gcagcgtcag atgctaatac       180
tggagaccgt ggacagacca ataatgctgc ttctgca                                217

<210> SEQ ID NO 16
<211> LENGTH: 206
<212> TYPE: DNA
<213> ORGANISM: Homo sapiens

<400> SEQUENCE: 16
gaccactgtg gcgctcttat acccgccgga cagacggtct agtgtttgtg gtggacgctg       60
cggaggctga gcggctggag gaagccaagg tggagttgca ccgaatcagc cgggcctcgg      120
acaaccaggg cgtgccagtg ctggtgctgg ccaacaagca ggaccagccc ggggcactga      180
gcgctgctga ggtggagaag aggctg                                            206
```

<210> SEQ ID NO 17
<211> LENGTH: 232
<212> TYPE: DNA
<213> ORGANISM: Homo sapiens

<400> SEQUENCE: 17

```
cgtcggagtt tcgaaagaag tggaataagt gggctctgag tcgtgggaag agggaactgc      60
ggatgtccag cagctacccc accgggctcg ctgacgtgaa ggccgggcct gcccagaccc     120
ttattcggcc ccaggacatg aaggtgcct ctcgaagccc cgaagacagc agtccggatg      180
ccgcccgcat ccgagtcaag cgctaccgcc agagcatgaa caacttccag gg             232
```

<210> SEQ ID NO 18
<211> LENGTH: 151
<212> TYPE: DNA
<213> ORGANISM: Homo sapiens

<400> SEQUENCE: 18

```
gtggcaaagg agcagagaac tttgacaagt tcttcacacg aggacagccc gtcttaacac      60
cacctgatca gctggttatt gctaacatag accagtctga ttttgaaggg ttctcgtatg     120
tcaaccccca gtttgtgcac cccatcttac a                                    151
```

<210> SEQ ID NO 19
<211> LENGTH: 228
<212> TYPE: DNA
<213> ORGANISM: Homo sapiens

<400> SEQUENCE: 19

```
tgaaggggag gatgaagatg aactcttcca atccatcatg gaacacaacg tagcctatcc      60
caagtctatg tccaaggaag ctgtggccat ctgcaaaggg ctgatgacca aacacccagg     120
caaacgtctg ggttgtggac ctgaaggcga acgtgatatc aaagagcatg cattttttccg    180
gtatattgat tgggagaaac ttgaacgcaa agagatccag ccccctta                  228
```

<210> SEQ ID NO 20
<211> LENGTH: 189
<212> TYPE: DNA
<213> ORGANISM: Homo sapiens

<400> SEQUENCE: 20

```
caactacatg agccccacct tctgtgacca ctgcggcagc ctgctctggg gactggtgaa      60
gcagggatta aagtgtgaag actgcggcat gaatgtgcac cataaatgcc gggagaaggt     120
ggccaacctc tgcggcatca accagaagct tttggctgag gccttgaacc aagtcaccca     180
gagagcctc                                                             189
```

<210> SEQ ID NO 21
<211> LENGTH: 195
<212> TYPE: DNA
<213> ORGANISM: Homo sapiens

<400> SEQUENCE: 21

```
aacggggagt ttgcttacct gtacagccag tgctacgagc tcaccaccaa cgaatacgtc      60
taccgcctct gccccttcaa gcttgtctcg cagaaaccca aactcggggg ctctcccacc     120
agccttggca cctggggctc atggattggc cccgaccacg acaagttcag tgccatgaag     180
tatgagcaag gcacg                                                      195
```

<210> SEQ ID NO 22
<211> LENGTH: 204
<212> TYPE: DNA
<213> ORGANISM: Homo sapiens

<400> SEQUENCE: 22
tgaggaccag cagtgtcttg tgttccgtga tgtggcccct caggctcctg tgcacttcct      60
ggtcattcct aagaagccca ttcctcggat tagccaggct gaagaagaag accagcagct     120
tctaggacac ctactccttg tggccaagca gacagcaaag gctgagggcc tgggagatgg     180
ataccgactt gtgatcaacg atgg                                            204

<210> SEQ ID NO 23
<211> LENGTH: 242
<212> TYPE: DNA
<213> ORGANISM: Homo sapiens

<400> SEQUENCE: 23
gctgactttg gtgtgagcaa tgaattcaag gcagtgacg cgctcctctc caactacgtg       60
ggcacgcccg ccttcatggc tcccgagtcg ctctctgaga cccgcaagat cttctctggg     120
aaggccaagg atgtttgggc catgggtgtg acactatact gctttgtctt tggccagtgc     180
ccattcatgg acgagcggat catgtgttta cacagtaaga tcaagagtca ggccctggaa     240
tt                                                                    242

<210> SEQ ID NO 24
<211> LENGTH: 203
<212> TYPE: DNA
<213> ORGANISM: Homo sapiens

<400> SEQUENCE: 24
attgccgagg tactggaatg caaataagaa ttcatcagat aggacctgga atggttcagc      60
aaattcagtc tgtgtgcatg gagtgccagg gccatgggga gcggatcagt cctaaagata     120
gatgtaaaag ctgcaacgga aggaagatag ttcgagagaa gaaaatttta gaagttcata     180
ttgacaaagg catgaaagat ggc                                             203

<210> SEQ ID NO 25
<211> LENGTH: 204
<212> TYPE: DNA
<213> ORGANISM: Homo sapiens

<400> SEQUENCE: 25
gttaaaaccc tgccaaacga aaccttcaca gactacccaa acaaatctt cagagtgaaa       60 accacacagt tctcctggac agaaatgctc attatgaagt gggtcttagg aatgatttgg     120
tccgaatgca aggaaatctg ggaggagggg ccacgggagt acgtgctgca cttgtggaac     180
ctgctagatt tcgggatgct gtcc                                            204

<210> SEQ ID NO 26
<211> LENGTH: 238
<212> TYPE: DNA
<213> ORGANISM: Homo sapiens

<400> SEQUENCE: 26
aaagaaacag aagcttgcca aggagagagc tgggctttcc aagttacctg accttaaaga      60
tgctgaagct gttcagaagt tcttccttga agaaatacag cttggtgaag agttactagc     120

```
tcaaggtgaa tatgagaagg gcgtagacca tctgacaaat gcaattgctg tgtgtggaca        180
gccacagcag ttactgcagg tcttacagca aactcttcca ccaccagtgt tccagatg          238

<210> SEQ ID NO 27
<211> LENGTH: 170
<212> TYPE: DNA
<213> ORGANISM: Homo sapiens

<400> SEQUENCE: 27
tgccttcagc agagtgaaga ctttctttca aatgaaggat cagctggaca acttgttgtt        60
aaaggagtcc ttgctggagg actttaaggg ttacctgggt tgccaagcct tgtctgagat        120
gatccagttt tacctggagg aggtgatgcc ccaagctgag aaccaagacc                   170

<210> SEQ ID NO 28
<211> LENGTH: 197
<212> TYPE: DNA
<213> ORGANISM: Homo sapiens

<400> SEQUENCE: 28
atcagtgcgt ccagggatac agggctctac acagaggtcc tgctgagagc gtctgcaaaa       60
tgacccacgg gaagacaagg tggacccagc cccagctcat atgcacaggt gaaatggaga      120
ccagtcagtt tccaggtgaa gagaagcctc aggcaagccc cgaaggccgt cctgagagtg       180
agacttcctg cctcgtc                                                      197

<210> SEQ ID NO 29
<211> LENGTH: 196
<212> TYPE: DNA
<213> ORGANISM: Homo sapiens

<400> SEQUENCE: 29
gctgcgtcca ggaagattag atagaaaaat acatattgat ttgccaaatg aacaagcaag       60
attagacata ctgaaaatcc atgcaggtcc cattacaaag catggtgaaa tagattatga      120
agcaattgtg aagctttcgg atggctttaa tggagcagat ctgagaaatg tttgtactga      180
agcaggtatg ttcgca                                                       196

<210> SEQ ID NO 30
<211> LENGTH: 177
<212> TYPE: DNA
<213> ORGANISM: Homo sapiens

<400> SEQUENCE: 30
atccctcatc acagcctcac agtttttcga gatctggctc catttcgacg ctgacggaag      60
tggttacctg gaaggaaagg agctgcagaa cttgatccag gagctccagc aggcgcgaaa      120
gaaggctgga ttggagttat cacctgaaat gaaaactttt gtggatcagt atgggca         177

<210> SEQ ID NO 31
<211> LENGTH: 241
<212> TYPE: DNA
<213> ORGANISM: Homo sapiens

<400> SEQUENCE: 31
tagcgtatgg tgctgctgtc caggctggtg tgctctctgg tgatcaagat acaggtgacc      60
tggtactgct tgatgtatgt ccccttacac ttggtattga aactgtggga ggtgtcatga      120
ccaaactgat tccaaggaac acagtggtgc ctaccaagaa gtctcagatc ttttctacag      180
```
cttctgataa tcaaccaact gttacaatca aggtctatga aggtgaaaga cccctgacaa    240
a                                                                   241

<210> SEQ ID NO 32
<211> LENGTH: 230
<212> TYPE: DNA
<213> ORGANISM: Homo sapiens

<400> SEQUENCE: 32
cttcactgtc gtgtcgctgt tgtggtgga gcgagcaggc cggcggaccc tgcacctcat     60
aggcctcgct ggcatggcgg gttgtgccat actcatgacc atcgcgctag cactgctgga   120
gcagctaccc tggatgtcct atctgagcat cgtggccatc tttggctttg tggccttctt   180
tgaagtgggt cctggcccca tcccatggtt catcgtggct gaactcttca               230

<210> SEQ ID NO 33
<211> LENGTH: 159
<212> TYPE: DNA
<213> ORGANISM: Homo sapiens

<400> SEQUENCE: 33
accggcttcc tcattacctt cttggctttt accttcttca aagtccctga acccgtggc     60 aggacttttg aggatatcac acgggccttt gaagggcagg cacacggtgc agatagatct   120
ggaaaggacg gcgtcatgga gatgaacagc atcgagcct                          159

<210> SEQ ID NO 34
<211> LENGTH: 199
<212> TYPE: DNA
<213> ORGANISM: Homo sapiens

<400> SEQUENCE: 34
ccctataccc catgatgtgc cccatggaac accccctttc tgctgacatc gccatggcca    60
cccgtgcaga tgaggacgga gacacgcctc tccatattgc tgtggtgcag ggtaacctgc   120
cagctgtgca ccggctggtc aacctcttcc agcagggggg ccgggagctc gacatctaca   180
acaacctacg gcagacacc                                                199

<210> SEQ ID NO 35
<211> LENGTH: 168
<212> TYPE: DNA
<213> ORGANISM: Homo sapiens

<400> SEQUENCE: 35
ggagcttcga gaacaactgg aacatttaca agctcctcac ccaccagaag ccccccaagg    60
agaagtctaa cttctccctg gccatcctga atgtggggc cccggcggct ggcatgaatg   120
cggccgtgcg ctcggcggtg cggaccggca tctcccatgg acacacag                168

<210> SEQ ID NO 36
<211> LENGTH: 206
<212> TYPE: DNA
<213> ORGANISM: Homo sapiens

<400> SEQUENCE: 36
caagctaact cgccctcaac tcccaactcg gctggttctt ccagttcttt taacatgtca    60
aactctggag atttgttcat gagcgtgcag tcactcaatg gggattctta ccaaggggcc   120
caggttggag ccaacgtgca atcacaggtg gatacccttc gccatgttat cagccagaca   180
ggaggataca gtgatggact cgcagc                                        206

<210> SEQ ID NO 37
<211> LENGTH: 247
<212> TYPE: DNA
<213> ORGANISM: Homo sapiens

<400> SEQUENCE: 37

```
gcacaagctt caggtcttcc aggcgctgcg gggcctgcag aggggcagtg ccgtcgtggg      60
ccagtaccag tcttacagtg agcaggtgcg cagagagctg cagaagccag acagcttcca     120
cagcctgacg ccgaccttcg cagccgtcct agtgcacatt gacaaccttc gctgggaggg     180
cgtgcctttc atcctgatgt ctggcaaagc cttggacgag agagtgggct acgctcggat     240
cttgttc                                                                247
```

<210> SEQ ID NO 38
<211> LENGTH: 179
<212> TYPE: DNA
<213> ORGANISM: Homo sapiens

<400> SEQUENCE: 38

```
cgcaaatacc aagtggacct gtccaagggc ctcaccaacc agcgggctca ggacgttctg      60
gctcgagatg ggcccaacgc cctcacacca cctcccacaa cccctgagtg ggtcaagttc     120
tgccgtcagc ttttcggggg gttctccatc ctgctgtgga ttgggctat cctctgctt      179
```

<210> SEQ ID NO 39
<211> LENGTH: 238
<212> TYPE: DNA
<213> ORGANISM: Homo sapiens

<400> SEQUENCE: 39

```
ctgtcagaga cagggtgcaa ttgtggctgt gaccggggat ggtgtgaacg actcccccgc      60
tctgaagaag gccgacattg gggtggccat gggcatcgct ggctctgacg tctccaagca     120
ggcagctgac atgatcctgc tggacgacaa ctttgcctcc atcgtcacag gggtggagga     180
gggccgcctg atcttcgaca acctaaagaa gtccattgcc tacaccctga ccagcaat      238
```

<210> SEQ ID NO 40
<211> LENGTH: 159
<212> TYPE: DNA
<213> ORGANISM: Homo sapiens

<400> SEQUENCE: 40

```
aaccaaccag caaaaccaag acaacttag aaaatcctga cttccgagaa atccgctcct       60
ttgtggagac gaaggctgac agcatcatca gacagaagcc cgtcgacctc ctgaagtaca     120
atcaaaaggg cctgacccgc gtctacccaa agggacaaa                             159
```

<210> SEQ ID NO 41
<211> LENGTH: 240
<212> TYPE: DNA
<213> ORGANISM: Homo sapiens

<400> SEQUENCE: 41

```
tgccacccat atctcactca ggagaagtta atccagtact gccagtccaa aggcatcgtg      60
gtgaccgcct acagccccct cggctctcct gacaggccct gggccaagcc cgaggaccct     120
tctctcctgg aggatcccag gatcaaggcg atcgcagcca agcacaataa aactacagcc     180
caggtcctga tccggttccc catgcagagg aacttggtgg tgatccccaa gtctgtgaca     240
```

```
<210> SEQ ID NO 42
<211> LENGTH: 245
<212> TYPE: DNA
<213> ORGANISM: Homo sapiens

<400> SEQUENCE: 42
cccgctaaat cccctagaag tcccactcct aaacacatcc gtattactcg catcaggagt      60
atcaatcacc tgagctcacc atagtctaat agaaaacaac cgaaaccaaa taattcaagc     120
actgcttatt acaattttac tgggtctcta ttttaccctc ctacaagcct cagagtactt     180
cgagtctccc ttcaccattt ccgacggcat ctacggctca acattttttg tagccacagg     240
cttcc                                                                 245

<210> SEQ ID NO 43
<211> LENGTH: 204
<212> TYPE: DNA
<213> ORGANISM: Homo sapiens

<400> SEQUENCE: 43
ggcactgaag gagaaggaga aggcctcctg gagcagcctc tccatggatg agaaagtcga      60
gttgtatcgc attaagttca aggagagctt tgctgagatg aacagggggct cgaacgagtg    120 gaagacggtt gtgggcggtg ccatgttctt catcggtttc accgcgctcg ttatcatgtg     180
gcagaagcac tatgtgtacg gccc                                            204

<210> SEQ ID NO 44
<211> LENGTH: 152
<212> TYPE: DNA
<213> ORGANISM: Homo sapiens

<400> SEQUENCE: 44
gcatgcagac ggttaaatga ttttgctagt ctagttcgaa tcctagaggt tgttaaggac      60
aaagcaggac ctcataagga aatctacccc tatgtcatcc aggaacttag accaacttta    120
aatgaactgg gaatctccac tccggaggaa ct                                   152

<210> SEQ ID NO 45
<211> LENGTH: 172
<212> TYPE: DNA
<213> ORGANISM: Homo sapiens

<400> SEQUENCE: 45
actgggttgg agagggagat catgctggct gcaaagaagg gactggaccc atacaatgta      60
ctggccccaa agggagcttc aggcaccagg gaagaccctt atttagtccc ctccatctcc    120
aacaagagaa tagtaggctg catctgtgaa gaggacaata ccagcgtcgt ct             172

<210> SEQ ID NO 46
<211> LENGTH: 193
<212> TYPE: DNA
<213> ORGANISM: Homo sapiens

<400> SEQUENCE: 46
atatggcaaa agcggacaag gcccgttatg aaagagaaat gaaaacctat atccctccca      60
aaggggagac aaaaaagaag ttcaaggatc ccaatgcacc caagaggcct ccttcggcct    120
tcttcctctt ctgctctgag tatcgcccaa aaatcaaagg agaacatcct ggcctgtcca    180
ttggtgatgt tgc                                                        193
```

```
<210> SEQ ID NO 47
<211> LENGTH: 248
<212> TYPE: DNA
<213> ORGANISM: Homo sapiens

<400> SEQUENCE: 47
ttccaagcca tggttaaagc tttagagaag gaagcagcca gtgagaagca gcagctggtg      60
gagacccacc tggcccgagt ggaagctatg ctgaatgacc gccgtcggat ggctctggag     120
aactacctgg ctgccttgca gtctgacccg ccacggcctc atcgcattct ccaggcctta     180
cggcgttatg tccgtgctga gaacaaagat cgcttacata ccatccgtca ttaccagcat     240
gtgttggc                                                              248

<210> SEQ ID NO 48
<211> LENGTH: 190
<212> TYPE: DNA
<213> ORGANISM: Homo sapiens

<400> SEQUENCE: 48
cctgaggatc cattccaaga actttcacga ggacacccct tagcagtacca aggccaaggg     60 ccacaacccc aggagttcca tagctgtcaa acttttttaag ttctccaggg aaaagaaagc    120
agctaagacg ttgggcattg tggtcggtat gttcatcttg tgctggctac ccttcttcat     180
cgctctaccg                                                            190

<210> SEQ ID NO 49
<211> LENGTH: 172
<212> TYPE: DNA
<213> ORGANISM: Homo sapiens

<400> SEQUENCE: 49
atagagggga accaggtgct gcattccttc acagctgtct gccaggatga tggcacgtgg      60
catcgtgcca tgcccagatg caagatcaag gactgtgggc agccccgaaa cctgcctaat     120
ggtgacttcc gttacaccac cacaatggga gtgaacacct acaaggcccg ta             172

<210> SEQ ID NO 50
<211> LENGTH: 165
<212> TYPE: DNA
<213> ORGANISM: Homo sapiens

<400> SEQUENCE: 50
cactagccag gtctcgaagg gctgcgtggc tcaggccccc aatgccatcc ttgaagtcca      60
tgtcctcttc ctggagttcc aacgggccc gtcacagctg agctgactc tccaggcatc     120 caagcaaaat ggcacctggc cccgagaggt gcttctggtc ctcag                     165

<210> SEQ ID NO 51
<211> LENGTH: 238
<212> TYPE: DNA
<213> ORGANISM: Homo sapiens

<400> SEQUENCE: 51
gagtcaacgg atttggtcgt attgggcgcc tggtcaccag ggctgctttt aactctggta      60
aagtggatat tgttgccatc aatgacccct tcattgacct caactacatg gtttacatgt    120
tccaatatga ttccacccat ggcaaattcc atggcaccgt caaggctgag aacgggaagc    180
ttgtcatcaa tggaaatccc atcaccatct tccaggagcg agatccctcc aaaatcaa      238
```

<210> SEQ ID NO 52
<211> LENGTH: 234
<212> TYPE: DNA
<213> ORGANISM: Homo sapiens

<400> SEQUENCE: 52
ggacttcgag caagagatgg ccacggctgc ttccagctcc tccctggaga agagctacga    60
gctgcctgac ggccaggtca tcaccattgg caatgagcgg ttccgctgcc ctgaggcact   120
cttccagcct tccttcctgg gcatggagtc ctgtggcatc cacgaaacta ccttcaactc   180
catcatgaag tgtgacgtgg acatccgcaa agacctgtac gccaacacag tgct          234

<210> SEQ ID NO 53
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 53
tcctggaatg agaccctcac                                                 20

<210> SEQ ID NO 54
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 54
gagacaccca ctcagcacaa                                                 20

<210> SEQ ID NO 55
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 55
gcttgctgaa aatggtcgat                                                 20

<210> SEQ ID NO 56
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 56
cggatcagtc ttagcctcca                                                 20

<210> SEQ ID NO 57
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 57
gcgggacttc agtcctagtg                                                 20

```
<210> SEQ ID NO 58
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 58
ctcgtgcttg agatgcttgt                                              20

<210> SEQ ID NO 59
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 59
gatcgtcttg tctggggaaa                                              20

<210> SEQ ID NO 60
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 60
ggtgactgcg ctgtctgata                                              20

<210> SEQ ID NO 61
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 61
ggcctgactg gcattgtatt                                              20

<210> SEQ ID NO 62
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 62
tggcgtaggt ttggtctagg                                              20

<210> SEQ ID NO 63
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 63
ttcagctctg catcgttttg                                              20

<210> SEQ ID NO 64
<211> LENGTH: 20
<212> TYPE: DNA
<213> ORGANISM: Artificial Sequence
<220> FEATURE:
<223> OTHER INFORMATION: chemically-synthesized PCR primer
```

<400> SEQUENCE: 64
tcttttggat gctctggtca                                        20

<210> SEQ ID NO 65
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 65
tcaaaggcct tggttctgac                                        20

<210> SEQ ID NO 66
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 66
gtgcaggcca aactggtaat                                        20

<210> SEQ ID NO 67
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 67
ctccccgaga aaatgatgaa                                        20

<210> SEQ ID NO 68
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 68
cacagaaagt ggctcgatca                                        20

<210> SEQ ID NO 69
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 69
ttcatgatca cgccctcata                                        20

<210> SEQ ID NO 70
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 70
taaaggatgc gtagggatgg                                        20

<210> SEQ ID NO 71
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 71
ccgaggtggt tttcatctgt                                               20

<210> SEQ ID NO 72
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 72
tccgccctat aagcatcttg                                               20

<210> SEQ ID NO 73
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 73
acatcgagat cgccacctac                                               20

<210> SEQ ID NO 74
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 74
atctccacgg tcttcaccac                                               20

<210> SEQ ID NO 75
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 75
cattccagcc ttggactcat                                               20

<210> SEQ ID NO 76
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 76
tcacaacctt tgttgggtca                                               20

<210> SEQ ID NO 77
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 77
ccaacccagt ggacattctt                                                   20

<210> SEQ ID NO 78
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 78
aaacacctgc cacattcaca                                                   20

<210> SEQ ID NO 79
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 79
cctgggagat tcatggaga                                                    20

<210> SEQ ID NO 80
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 80
gtgcccactg tgtcattcac                                                   20

<210> SEQ ID NO 81
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 81
attacgggac ccaaatgtca                                                   20

<210> SEQ ID NO 82
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 82
tgcagaagca gcattattgg                                                   20

<210> SEQ ID NO 83
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 83
gaccactgtg gcgctcttat                                                   20

```
<210> SEQ ID NO 84
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 84
cagcctcttc tccacctcag                                              20

<210> SEQ ID NO 85
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 85
cgtcggagtt tcgaaagaag                                              20

<210> SEQ ID NO 86
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 86
ccctggaagt tgttcatgct                                              20

<210> SEQ ID NO 87
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 87
gtggcaaagg agcagagaac                                              20

<210> SEQ ID NO 88
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 88
tgtaagatgg ggtgcacaaa                                              20

<210> SEQ ID NO 89
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 89
tgaaggggag gatgaagatg                                              20

<210> SEQ ID NO 90
<211> LENGTH: 20
<212> TYPE: DNA
<213> ORGANISM: Artificial Sequence
<220> FEATURE:
<223> OTHER INFORMATION: chemically-synthesized PCR primer
```

```
<400> SEQUENCE: 90
taagggggct ggatctcttt                                               20

<210> SEQ ID NO 91
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 91
caactacatg agccccacct                                               20

<210> SEQ ID NO 92
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 92
gaggctctct gggtgacttg                                               20

<210> SEQ ID NO 93
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 93
aacggggagt ttgcttacct                                               20

<210> SEQ ID NO 94
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 94
cgtgccttgc tcatacttca                                               20

<210> SEQ ID NO 95
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 95
tgaggaccag cagtgtcttg                                               20

<210> SEQ ID NO 96
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 96
ccatcgttga tcacaagtcg                                               20
```

```
<210> SEQ ID NO 97
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 97
gctgactttg gtgtgagcaa                                              20

<210> SEQ ID NO 98
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 98
aattccaggg cctgactctt                                              20

<210> SEQ ID NO 99
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 99
attgccgagg tactggaatg                                              20

<210> SEQ ID NO 100
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 100
gccatctttc atgcctttgt                                              20

<210> SEQ ID NO 101
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 101
gttaaaaccc tgccaaacga                                              20

<210> SEQ ID NO 102
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 102
ggacagcatc ccgaaatcta                                              20

<210> SEQ ID NO 103
<211> LENGTH: 20
<212> TYPE: DNA
<213> ORGANISM: Artificial Sequence
<220> FEATURE:
<223> OTHER INFORMATION: chemically-synthesized PCR primer
```

```
<400> SEQUENCE: 103
aaacagaagc ttgccaagga                                              20

<210> SEQ ID NO 104
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 104
catctggaac actggtggtg                                              20

<210> SEQ ID NO 105
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 105
tgccttcagc agagtgaaga                                              20

<210> SEQ ID NO 106
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 106
ggtcttggtt ctcagcttgg                                              20

<210> SEQ ID NO 107
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 107
atcagtgcgt ccagggatac                                              20

<210> SEQ ID NO 108
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 108
gacgaggcag gaagtctcac                                              20

<210> SEQ ID NO 109
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 109
gctgcgtcca ggaagattag                                              20
```

```
<210> SEQ ID NO 110
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 110
tgcgaacata cctgcttcag                                               20

<210> SEQ ID NO 111
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 111
atccctcatc acagcctcac                                               20

<210> SEQ ID NO 112
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 112
tgcccatact gatccacaaa                                               20

<210> SEQ ID NO 113
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 113
tagcgtatgg tgctgctgtc                                               20

<210> SEQ ID NO 114
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 114
tttgtcaggg gtctttcacc                                               20

<210> SEQ ID NO 115
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 115
cttcactgtc gtgtcgctgt                                               20

<210> SEQ ID NO 116
<211> LENGTH: 20
<212> TYPE: DNA
<213> ORGANISM: Artificial Sequence
<220> FEATURE:
<223> OTHER INFORMATION: chemically-synthesized PCR primer
```

<400> SEQUENCE: 116
tgaagagttc agccacgatg                                              20

<210> SEQ ID NO 117
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 117
accggcttcc tcattaccctt                                             20

<210> SEQ ID NO 118
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 118
aggctcgatg ctgttcatct                                              20

<210> SEQ ID NO 119
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 119
ccctataccc catgatgtgc                                              20

<210> SEQ ID NO 120
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 120
ggtgtctgcc gtaggttgtt                                              20

<210> SEQ ID NO 121
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 121
ggagcttcga gaacaactgg                                              20

<210> SEQ ID NO 122
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 122
ctgtgtgtcc atgggagatg                                              20

```
<210> SEQ ID NO 123
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 123
caagctaact cgccctcaac                                                 20

<210> SEQ ID NO 124
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 124
gctgcgagtc catcactgta                                                 20

<210> SEQ ID NO 125
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 125
gcacaagctt caggtcttcc                                                 20

<210> SEQ ID NO 126
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 126
gaacaagatc cgagcgtagc                                                 20

<210> SEQ ID NO 127
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 127
cgcaaatacc aagtggacct                                                 20

<210> SEQ ID NO 128
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 128
aagcagagga tagccccaat                                                 20

<210> SEQ ID NO 129
<211> LENGTH: 20
<212> TYPE: DNA
<213> ORGANISM: Artificial Sequence
<220> FEATURE:
<223> OTHER INFORMATION: chemically-synthesized PCR primer
```

<400> SEQUENCE: 129
ctgtcagaga cagggtgcaa                                              20

<210> SEQ ID NO 130
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 130
attgctggtc agggtgtagg                                              20

<210> SEQ ID NO 131
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 131
aaccaaccag caaaaccaag                                              20

<210> SEQ ID NO 132
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 132
tttgtccctt tgggtagacg                                              20

<210> SEQ ID NO 133
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 133
tgccacccat atctcactca                                              20

<210> SEQ ID NO 134
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 134
tgtcacagac ttggggatca                                              20

<210> SEQ ID NO 135
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 135
cccgctaaat cccctagaag                                              20

<210> SEQ ID NO 136
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 136
ggaagcctgt ggctacaaaa                                             20

<210> SEQ ID NO 137
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 137
ggcactgaag gagaaggaga                                             20

<210> SEQ ID NO 138
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 138
gggccgtaca catagtgctt                                             20

<210> SEQ ID NO 139
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 139
gcatgcagac ggttaaatga                                             20

<210> SEQ ID NO 140
<211> LENGTH: 19
<212> TYPE: DNA
<213> ORGANISM: Artificial Sequence
<220> FEATURE:
<223> OTHER INFORMATION: chemically-synthesized PCR primer

<400> SEQUENCE: 140
agttcctccg gagtggaga                                              19

<210> SEQ ID NO 141
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 141
actgggttgg agagggagat                                             20

<210> SEQ ID NO 142
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 142
agacgacgct ggtattgtcc                                              20

<210> SEQ ID NO 143
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 143
atatggcaaa agcggacaag                                              20

<210> SEQ ID NO 144
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 144
gcaacatcac caatggacag                                              20

<210> SEQ ID NO 145
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 145
ttccaagcca tggttaaagc                                              20

<210> SEQ ID NO 146
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 146
gccaacacat gctggtaatg                                              20

<210> SEQ ID NO 147
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 147
cctgaggatc cattccaaga                                              20

<210> SEQ ID NO 148
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 148
cggtagagcg atgaagaagg                                              20

-continued

```
<210> SEQ ID NO 149
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 149
atagagggga accaggtgct                                                    20

<210> SEQ ID NO 150
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 150
tacgggcctt gtaggtgttc                                                    20

<210> SEQ ID NO 151
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 151
cactagccag gtctcgaagg                                                    20

<210> SEQ ID NO 152
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 152
ctgaggacca gaagcacctc                                                    20

<210> SEQ ID NO 153
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 153
gagtcaacgg atttggtcgt                                                    20

<210> SEQ ID NO 154
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 154
ttgattttgg agggatctcg                                                    20

<210> SEQ ID NO 155
<211> LENGTH: 20
<212> TYPE: DNA
<213> ORGANISM: Artificial Sequence
<220> FEATURE:
<223> OTHER INFORMATION: chemically-synthesized PCR primer
```

```
<400> SEQUENCE: 155
ggacttcgag caagagatgg                                               20

<210> SEQ ID NO 156
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 156
agcactgtgt tggcgtacag                                               20
```